US009642519B2

(12) United States Patent
Imamura

(10) Patent No.: US 9,642,519 B2
(45) Date of Patent: May 9, 2017

(54) IMAGE PROCESSING APPARATUS AND CONTROL METHOD OF IMAGE PROCESSING APPARATUS

(71) Applicant: CANON KABUSHIKI KAISHA, Tokyo (JP)

(72) Inventor: Hiroshi Imamura, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/843,248

(22) Filed: Sep. 2, 2015

(65) Prior Publication Data
US 2016/0066779 A1 Mar. 10, 2016

(30) Foreign Application Priority Data

Sep. 5, 2014 (JP) ................. 2014-181342

(51) Int. Cl.
*A61B 3/10* (2006.01)
*A61B 3/14* (2006.01)
(Continued)

(52) U.S. Cl.
CPC .......... *A61B 3/0025* (2013.01); *A61B 3/0041* (2013.01); *A61B 3/0091* (2013.01); *A61B 3/1005* (2013.01); *A61B 3/1015* (2013.01); *A61B 3/1025* (2013.01); *A61B 3/1241* (2013.01); *A61B 3/14* (2013.01); *G06K 9/00604* (2013.01); *G06K 9/46* (2013.01); *G06K 9/4661* (2013.01); *G06K 9/6215* (2013.01); *G06T 7/0012* (2013.01); *G06T 7/0042* (2013.01);
(Continued)

(58) Field of Classification Search
USPC .................................. 351/200–246
See application file for complete search history.

(56) References Cited

U.S. PATENT DOCUMENTS 7,443,541 B2 * 10/2008 Mizutani .............. H04N 1/4057
358/3.02
2012/0229764 A1 9/2012 Tomatsu
2015/0181159 A1 * 6/2015 Matsuyama ......... H04N 7/0145
382/191

FOREIGN PATENT DOCUMENTS

CN 102209488 A 10/2011
CN 102670168 A 9/2012
(Continued)

OTHER PUBLICATIONS

Search Report;, Federal Service on Industrial Property; Federal State Budget Institution "Federal Institute of Industrial Property" (FIIP); pp. 1-2, Oct. 13, 2015.
(Continued)

*Primary Examiner* — Mohammed Hasan
(74) *Attorney, Agent, or Firm* — CANON USA, INC. IP Division

(57) ABSTRACT

An image processing apparatus generates one image by using at least one frame each of a plurality of moving images obtained by taking moving images of a plurality of different regions of an eye at different times. The apparatus includes a deciding unit configured to decide the at least one frame in each of the plurality of moving images, so that regions which have actually been shot are included in the plurality of moving images in the plurality of regions; and an image generating unit configured to generate one image by using the at least one frames decided from each of the plurality of moving images.

17 Claims, 14 Drawing Sheets

(51) Int. Cl.
    *A61B 3/00*     (2006.01)
    *A61B 3/12*     (2006.01)
    *G06K 9/00*     (2006.01)
    *G06K 9/46*     (2006.01)
    *G06K 9/62*     (2006.01)
    *G06T 7/00*     (2017.01)

(52) U.S. Cl.
    CPC ............... *G06K 2009/4666* (2013.01); *G06T 2207/30041* (2013.01)

(56) References Cited

FOREIGN PATENT DOCUMENTS

| | | |
|---|---|---|
| JP | 2012-213513 A | 11/2012 |
| JP | 2013-169309 A | 9/2013 |
| RU | 2011123636 A | 12/2012 |
| WO | 2013/125546 A1 | 8/2013 |

OTHER PUBLICATIONS

Office Action of Substantive Examination; Federal State Budget Institution "Federal Institute of Industrial Property" (FIIP); pp. 1-6, Oct. 2015.

\* cited by examiner

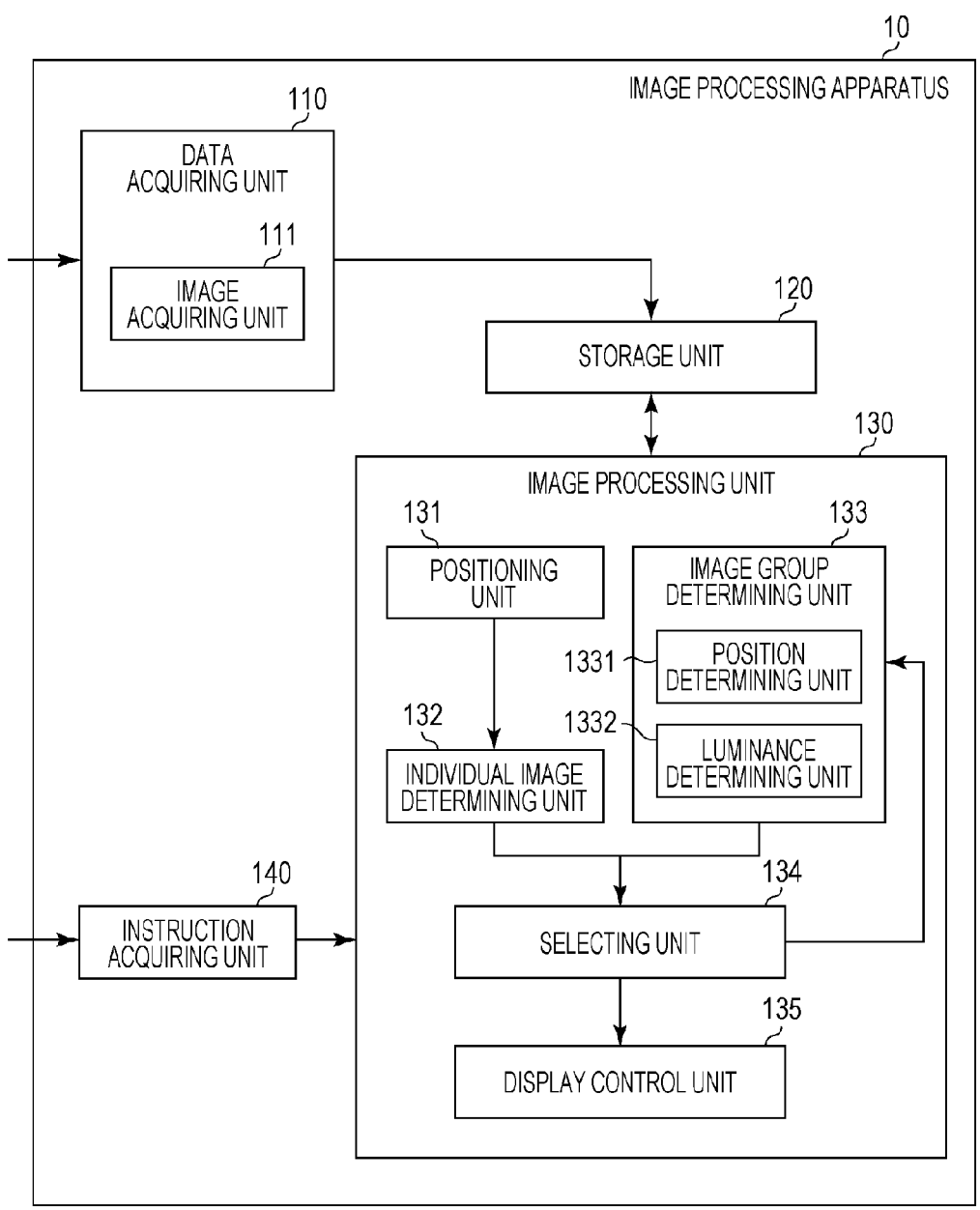

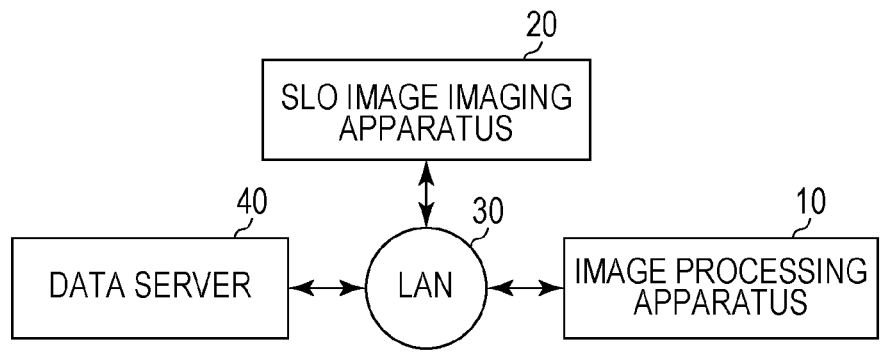
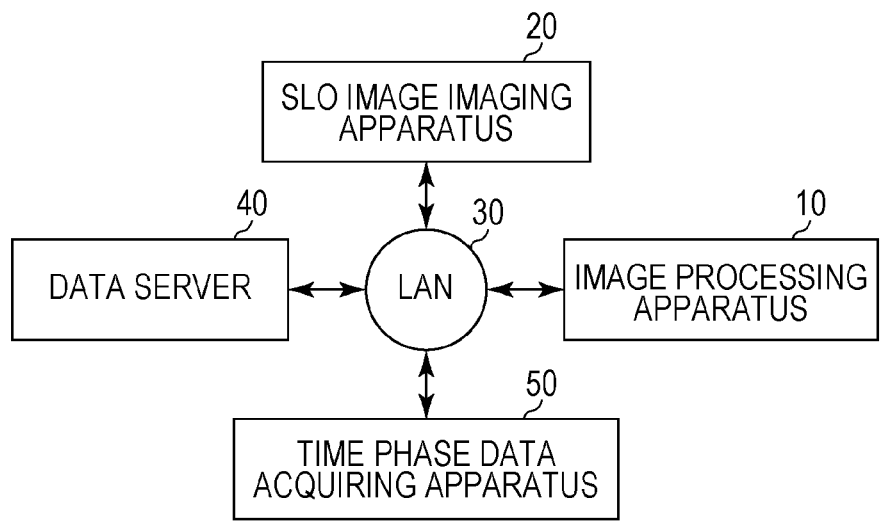
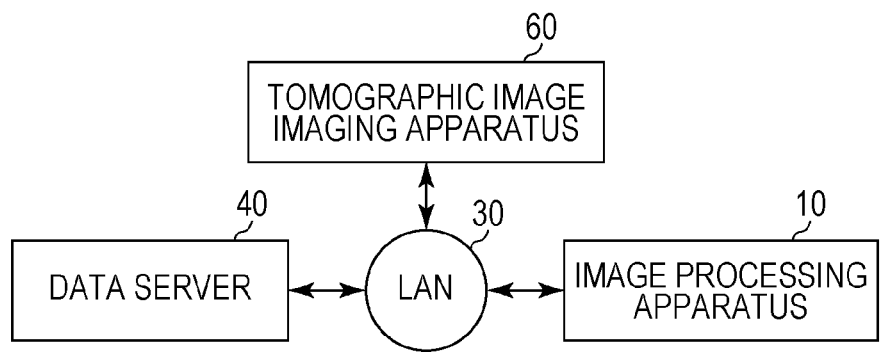

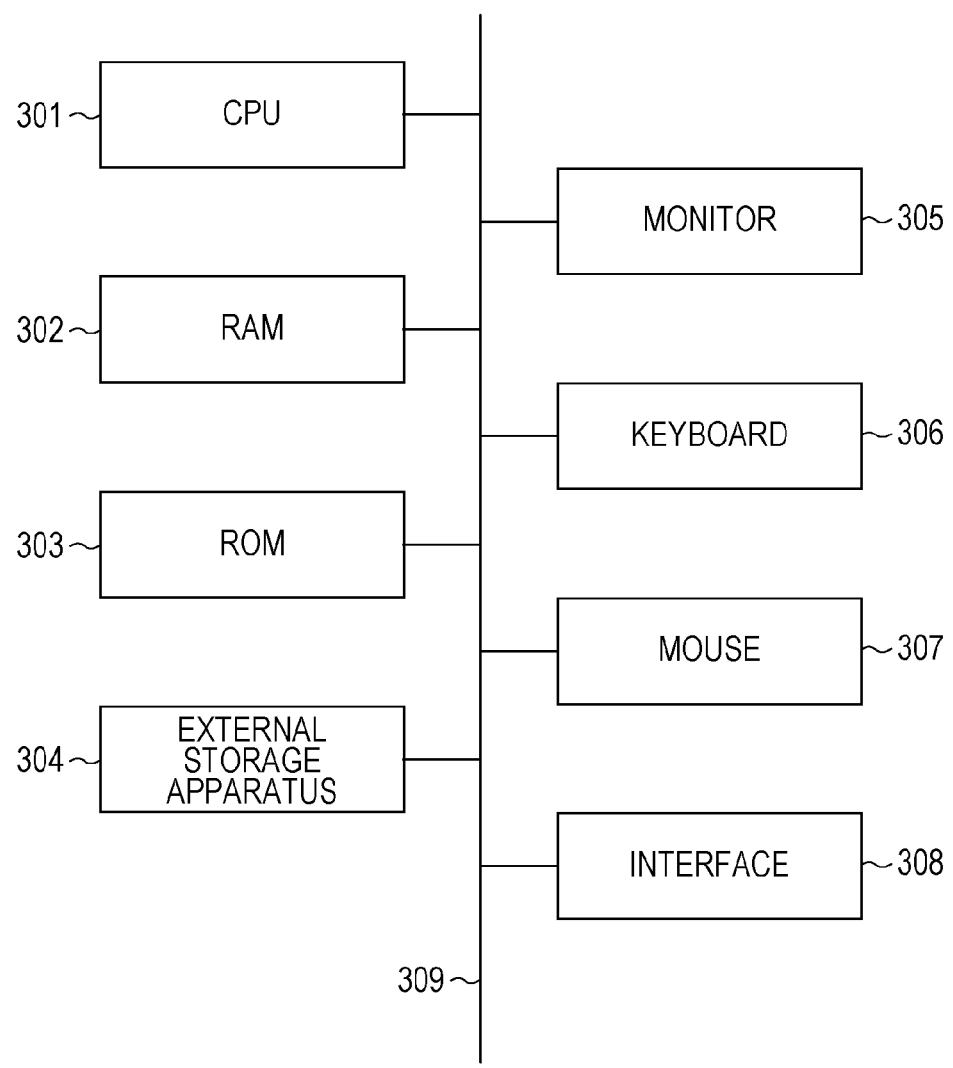

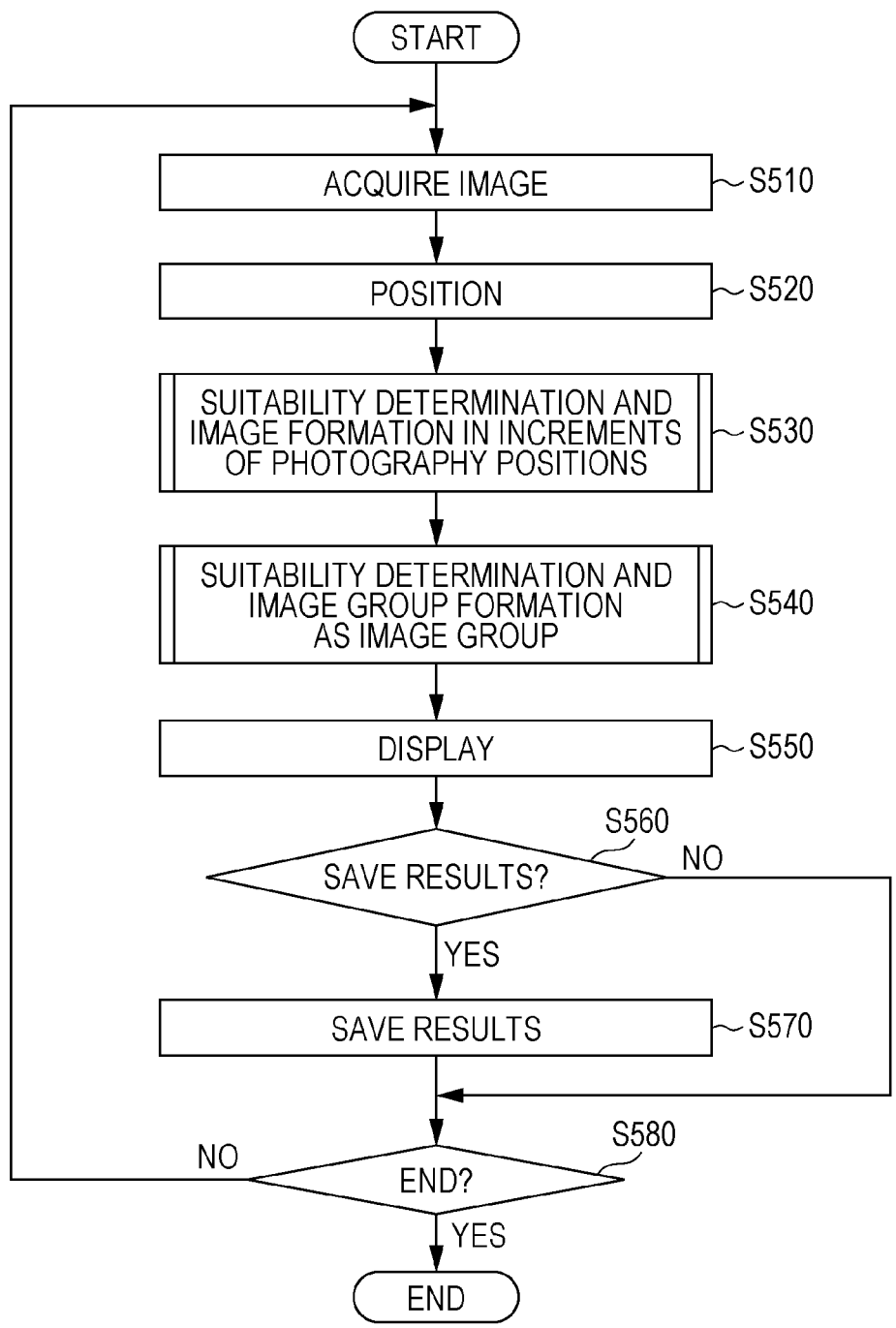

FIG. 6A
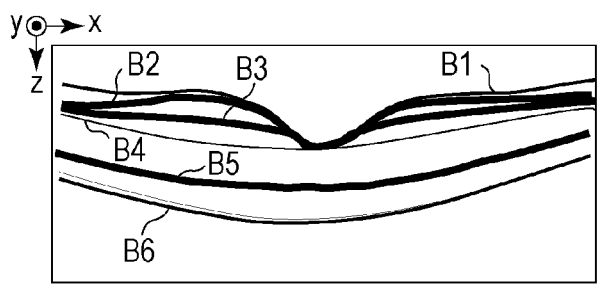
FIG. 6B
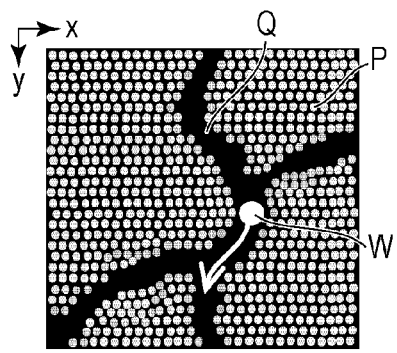
FIG. 6C  FIG. 6D  FIG. 6E  FIG. 6F
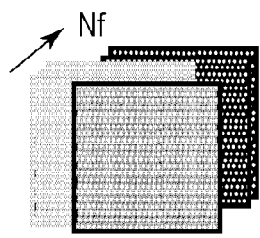 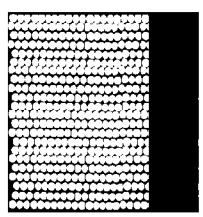 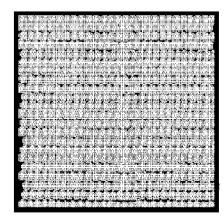 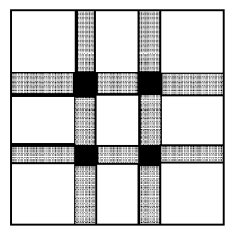
FIG. 6G  FIG. 6H
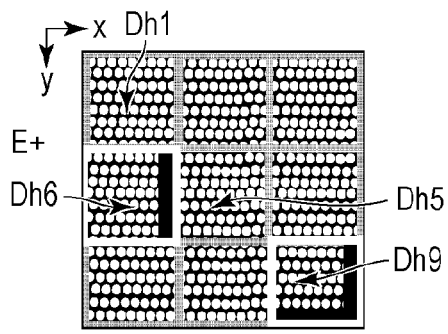 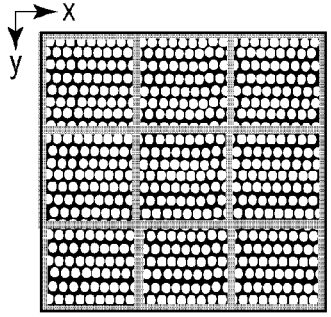
FIG. 6I  FIG. 6J
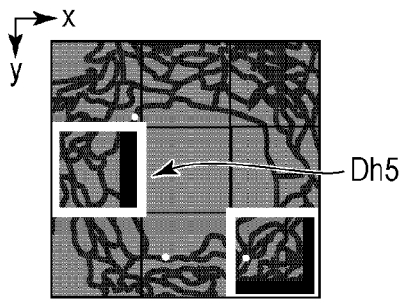 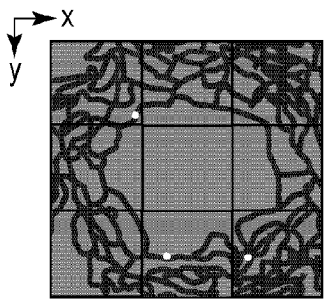

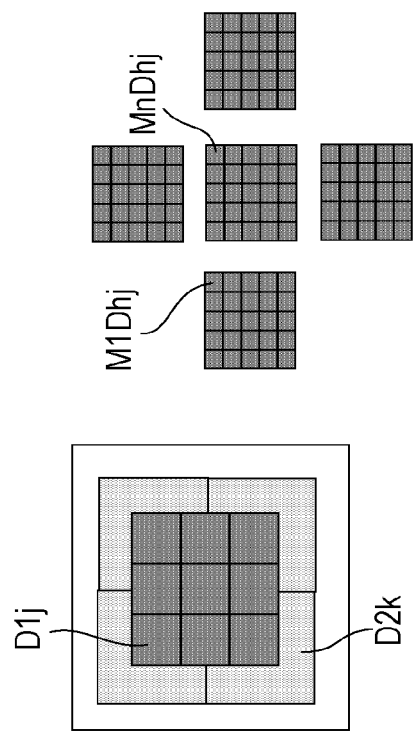
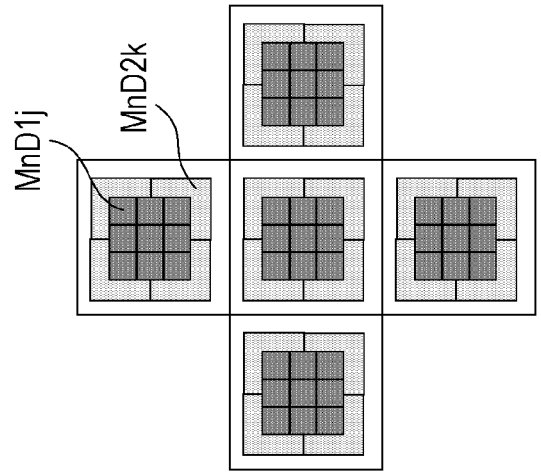
FIG. 14A  FIG. 14B  FIG. 14C

IMAGE PROCESSING APPARATUS AND CONTROL METHOD OF IMAGE PROCESSING APPARATUS

BACKGROUND OF THE INVENTION

Field of the Invention

The present invention relates to an image processing apparatus used in opthalmological diagnosis and treatment, and to a control method of the image processing apparatus.

Description of the Related Art

Examination of the eye is widely performed for early diagnosis and treatment of lifestyle diseases and diseases which are primary causes of loss of eyesight. The scanning laser opthalmoscope (SLO), which is an opthalmological apparatus that employs the principle of confocal laser scanning microscopy, performs raster scanning of a laser, which is measurement light, over the fundus, and acquires a high-resolution planar image from the intensity of returning light at high speed. An apparatus which images such a planar image will hereinafter be referred to as an SLO apparatus, and the planar image to as an SLO image.

In recent years, increased beam diameter of measurement light in SLO apparatuses has enabled acquisition of SLO images of the retina, with improved horizontal resolution. However, the increased beam diameter of the measurement light has led to a problem of deterioration the S/N ratio and the resolution of the SLO image during acquisition of SLO images of the retina, due to aberration of the eye being examined. An adaptive optic SLO apparatus has been developed to solve this problem. The adaptive optic SLO apparatus has an adaptive optic system that measures aberration of the eye being examined in real time using a wavefront sensor, and corrects aberration occurring in the eye being examined with regard to the measurement light and the returning light thereof using a wavefront correction device. This enables SLO images with high horizontal resolution (high-magnification image) to be acquired.

Such high-magnification images can be acquired as moving images, and are used for non-invasive observation of hemodynamic states. Retinal blood vessels are extracted from each frame, and the movement speed of blood cells through the capillaries, and so forth, are measured. Photoreceptors P are detected and the density distribution and array of the photoreceptors P measured, to evaluate the relationship with visual functions, using high-magnification images. FIG. 6B shows an example of a high-magnification image. The photoreceptors P, a low-luminance region Q corresponding to the position of capillaries, and a high-luminance region W corresponding to the position of a white blood cell, can be observed.

In a case of observing photoreceptors P or measuring distribution of photoreceptors P using a high-magnification image, the focus position is set nearby the outer layer of the retina (B5 in FIG. 6A) to take a high-magnification image such as in FIG. 6B. On the other hand, there are retinal blood vessels and capillaries that have branched running through the inner layers of the retinal (B2 through B4 in FIG. 6B). In cases of taking photographs of the eye to be examined, image region to be imaged may be larger than the angle of view high-magnification image. Cases of imaging widespread photoreceptor defect regions, cases of imaging a parafovea region which is an area of predilection for early-stage capillary lesions, and so forth, fall under such cases. Accordingly, Japanese Patent Laid-Open No. 2012-213513 discloses a technology to composite and display multiple high-magnification images acquired by shooting at different shooting positions.

Also, Japanese Patent Laid-Open No. 2013-169309 discloses a technology in which exceptional frames where effects of ocular microtremor in a high-magnification moving image of a certain shooting position are determined, and just the frames other than the exceptional frames determined in the high-magnification moving image are displayed.

SUMMARY OF THE INVENTION

An image processing apparatus generates one image by using at least one frame each of a plurality of moving images obtained by taking moving images of a plurality of different regions of an eye at different times. The apparatus includes a deciding unit configured to decide the at least one frame in each of the plurality of moving images, so that regions which have actually been shot are included in the plurality of moving images in the plurality of regions; and an image generating unit configured to generate one image by using the at least one frames decided from each of the plurality of moving images.

Further features of the present invention will become apparent from the following description of exemplary embodiments with reference to the attached drawings.

BRIEF DESCRIPTION OF THE DRAWINGS

FIG. 1 is a block diagram illustrating a functional configuration example of an image processing apparatus according to a first embodiment of the present invention.

FIGS. 2A through 2C are block diagrams illustrating configuration examples of a system including the image processing apparatus according to an embodiment of the present invention.

FIG. 4 is a block diagram illustrating a hardware configuration example of a computer which has hardware equivalent to a storage unit and image processing unit and holds other units as software which is executed.

FIG. 5 is a flowchart of processing which the image processing apparatus according to an embodiment of the present invention executes.

FIGS. 6A through 6J are diagrams illustrating what is performed in image processing according to the first embodiment of the present invention.

FIGS. 14A through 14C are diagrams illustrating what is performed in image processing according to another embodiment of the present invention.

DESCRIPTION OF THE EMBODIMENTS

Figure 3:
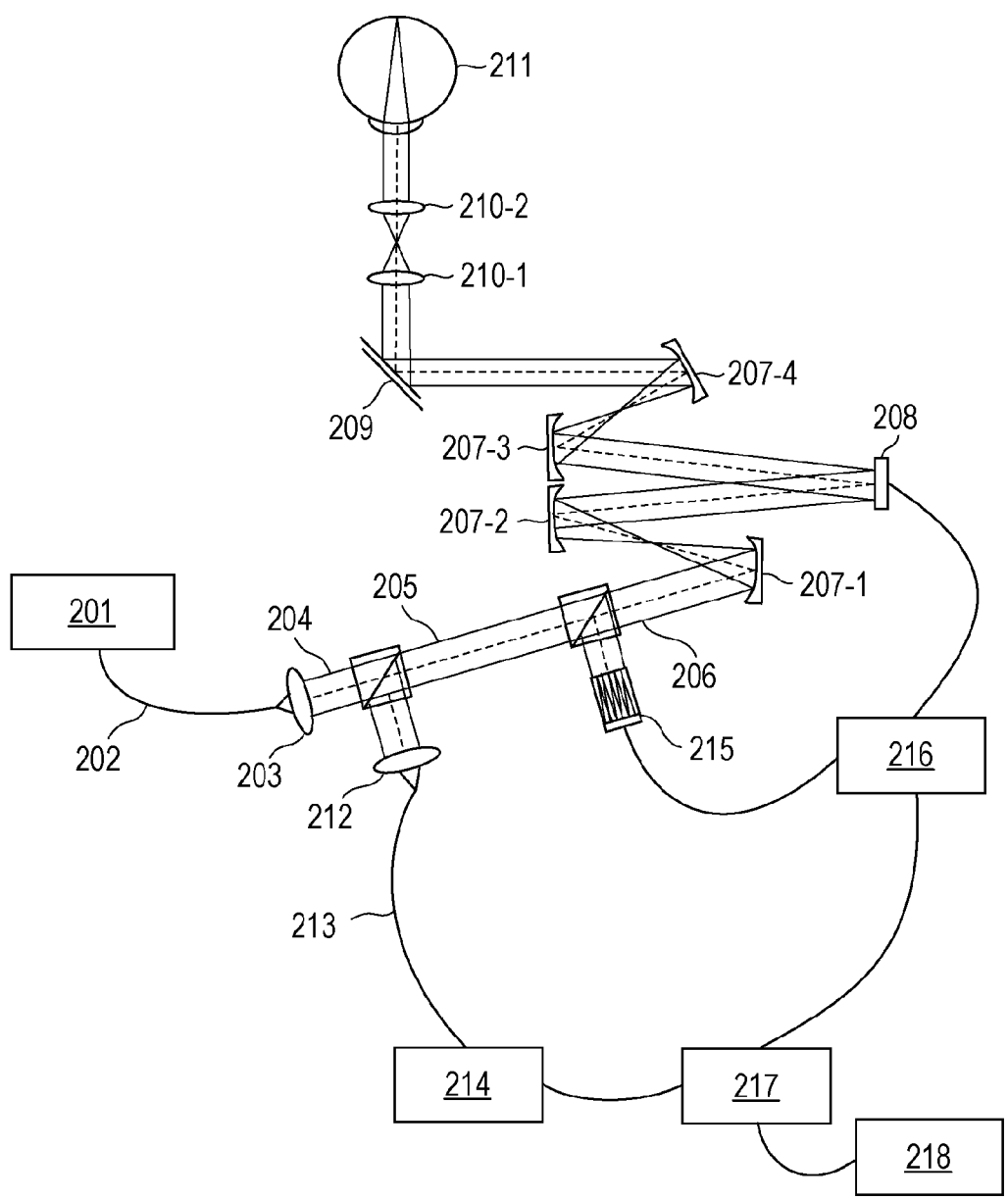
FIG. 3 is a diagram for describing the overall configuration of an SLO image imaging apparatus according to an embodiment of the present invention.

Now, a case will be considered where a certain frame is selected from each of multiple high-magnification moving images acquired by shooting at different shooting positions, and the selected frames are composited (montaged). Several frames are generally selected from the frames of the multiple high-magnification moving images, and the selected frames are used to acquire a representative image. The acquired representative images are composited, thereby generating a wide-range image. There have been cases where the continuance in adjacent representative images was not good with regard to shooting position, luminance properties, image properties, and so forth, when adjacent representative images were compared with each other. There were cases where unanalyzable regions occurred, regions for analysis could not be extracted, and so forth, when measuring the distribution of cell groups, tissues, and lesions thereof (photoreceptor defects, microaneurysms) distributed over a wide area, using such wide-range images.

There has been found to be demand for selecting images when acquiring representative images of each of multiple high-magnification moving images acquired by shooting at different shooting positions, so that the continuity of the representative images is improved.

The image processing apparatus according to the present embodiment has a selecting unit (e.g., selecting unit 134 in FIG. 1) that selects images from each of multiple moving images that have been taken at different positions of the eye, based on continuity of properties of multiple images (an image group) made up of images (representative images) acquired by selecting from each of the multiple moving images. Accordingly, when acquiring representative images from each of multiple high-magnification moving images shot at different shooting positions, images can be selected so that the continuity among the representative images is better.

Now, properties of multiple images (an image group) are, for example, at least one of the relative position, luminance properties, and image properties, of the multiple images. Each image (image acquired by being selected from a moving image) of the multiple images (image group) is a representative image acquired from the moving image, and may be one image selected from a moving image, or may be multiple images with relatively little noise, artifacts, and so forth, which are selected and overlaid. In a case of using overlaid images, the number of overlaid images is preferably small, so that the continuity among the properties of the multiple images will be high. Also preferably further provided is a determining unit, to determine a value indicating continuity, whereby an image can be selected from a moving image so that the determined value satisfies predetermined conditions. A case where a determined value satisfies predetermined conditions here is, for example, a case where the determined value exceeds a threshold value, or is greatest. A value indicating continuity is preferably determined using a composited image where multiple images have been composited. For example, determination is made based on at least one of the area of the composited image and the length of avascular area boundary, which will be described in detail in the embodiments. Preferred embodiments of the image processing apparatus according to the present invention and the operation method thereof will be described below in detail with reference to the attached drawings. Note however, that the present invention is not restricted to these.

Also, it is difficult to acquire images with no image distortion in any of the images when consecutively shooting at multiple shooting positions. Accordingly, generally, high-magnification moving image shooting is performed of a certain shooting position of the eye. Now, Japanese Patent Laid-Open No. 2012-213513 discloses that shooting may be performed multiple times at the same position, and that images used to configure a panorama image may be selected such that images with the best correlation with adjacent images are selected. Now, there have been problems of incomplete images in the panorama image if just images optimal to configure a panorama image are selected from multiple images. Accordingly, an image processing apparatus according to another embodiment selects multiple frames from moving images, so that incomplete images in the panorama image are minimized. Accordingly, incomplete images in the panorama image can be reduced.

Preferred embodiments of the image processing apparatus according to the present invention and the operation method thereof will be described below in detail with reference to the attached drawings. Note however, that that the present invention is not restricted to these.

First Embodiment

Continuity of Relative Position or Luminance Properties of Multiple Images of Different Positions The image processing apparatus according to a first embodiment determines suitability of an image group based on continuity of at least one of relative position and luminance properties of multiple images (an image group) at different positions. This configuration has been made so that a region of photography can be observed under generally the same conditions, by selecting, compositing, and displaying frames or images with the highest suitability.

Specifically, description will be made regarding a case where an image group is made up of nine high-magnification images such as illustrated in FIG. 6G, an overlaid image is generated using frames selected by a selecting unit in increments of the shooting positions, the overlaid images are composited, and the suitability as an image group is determined.

Overall Configuration

FIG. 2A is a configuration diagram of a system including the image processing apparatus 10 according to the present embodiment. The image processing apparatus 10 is connected to an SLO image imaging apparatus 20 and data server 40 via a local area network (LAN) 30 including optical fiber, Universal Serial Bus (USB), IEEE 1394, or the like, as illustrated in FIG. 2. The configuration of connection to these devices may be via an external network such as the Internet, or may be a configuration where the image processing apparatus 10 is directly connected to the SLO image imaging apparatus 20.

First, the SLO image imaging apparatus 20 is an apparatus to shoot wide-angle images D1 and high-magnification images Dh of the eye. The SLO image imaging apparatus 20 transmits wide-angle images D1, high-magnification images Dh, and information of fixation target positions F1 and Fh used for shooting thereof, to the image processing apparatus 10 and the data server 40. In a case where images at each magnification are acquired at different shooting positions, this is expressed as D1I, Dhj. That is to say, i and j are variables indicating the numbers for the shooting positions, where i=1, 2, . . . , imax, and j=1, 2, . . . , jmax. In a case of acquiring high-magnification images at different magnifications, this is expressed like D1j, D2k, . . . , in order from the highest-magnification image, with D1j denoting a high-magnification image and D2k denoting a mid-magnification image.

The data server 40 holds the wide-angle images D1 and high-magnification images Dh of the eye, shooting conditions data such as fixation target positions F1 and Fh used for the shooting thereof, image features of the eye, normal values relating to distribution of the image features of the eye, and so forth. In the present invention, image features relating to the photoreceptors P, capillaries Q, blood cells W, retinal blood vessels, and retina layer boundary, are handled as image features of the eye. The wide-angle images D1, high-magnification images Dh output from the SLO image imaging apparatus 20, fixation target positions F1 and Fh used for the shooting thereof, and image features of the eye output from the image processing apparatus 10, are saved in the server. Also, the wide-angle images D1, high-magnification images Dh, image features of the eye, and normal value DATA of image features of the eye, are transmitted to the image processing apparatus 10 in response to requests from the image processing apparatus 10.

Next, the functional configuration of the image processing apparatus 10 according to the present embodiment will be described with reference to FIG. 1. FIG. 1 is a block diagram illustrating the functional configuration of the image processing apparatus 10. The image processing apparatus 10 includes a data acquiring unit 110, a storage unit 120, an image processing unit 130, and an instruction acquiring unit 140. The data acquiring unit 110 includes an image acquiring unit 111. The image processing unit 130 includes a positioning unit 131, an individual image determining unit 132, an image group determining unit 133, the selecting unit 134, and a display control unit 135. Further, the image group determining unit 133 includes a position determining unit 1331 and a luminance determining unit 1332.

SLO Image Imaging Apparatus that has Adaptive Optic System

Next, the configuration of the SLO image imaging apparatus 20 that has an adaptive optic system will be described with reference to FIG. 3. First, 201 denotes a light source, for which a super luminescent diode (SLD) light source was used. Although the light source is shared between fundus imaging and wavefront measurement in the present embodiment, a configuration may be made where these are separate light sources that are multiplexed along the way. Light irradiated from the light source 201 passes through a single-mode optic fiber 202 and is irradiated as parallel measurement light 205 from a collimator 203. The irradiated measurement light 205 is transmitted through a light splitting unit 204 made up of a beam splitter, and is guided to an optical system of the adaptive optic system.

The adaptive optic system is made up of a light splitting unit 206, a wavefront sensor 215, a wavefront correcting device 208, and reflecting mirrors 207-1 through 207-4 for guiding light thereto. The reflecting mirrors 207-1 through 207-4 are installed so that at least the pupil of the eye, the wavefront sensor 215, and the wavefront correcting device 208 are optically in a conjugate relationship. A beam splitter is used in the present embodiment as the light splitting unit 206. Also, a spatial phase modulator using a liquid crystal device is employed as the wavefront correcting device 208 in the present embodiment. Note that a variable shape mirror may be used as the wavefront correcting device. Light that has passed through the adaptive optic system is scanned one-dimensionally or two-dimensionally by a scanning optical system 209. As the scanning optical system 209, two Galvano scanners were used in the present embodiment of main scanning (fundus horizontal direction) and sub-scanning (fundus vertical direction). A resonance scanner may be used for the main scanning side of the scanning optical system 209 for higher speed shooting. An eye 211 is scanned by the measurement light 205 scanned by the scanning optical system 209, via eyepiece lenses 210-1 and 210-2. The measurement light 205 by which the eye 211 is irradiated is reflected or scattered at the fundus. Optimal irradiation for the eyepiece visibility of the eye 211 can be realized by adjusting the position of the eyepiece lenses 210-1 and 210-2. Although eyepiece lenses are used here, sphere mirrors or the like may be used for the configuration.

Part of the reflected/scattered light (returning light) reflected from or scattered at the retina of the eye 211 travels along the same path as it came when input but in the opposite direction, and is reflected at the wavefront sensor 215 by the light splitting unit 206 to be used to measure the beam wavefront. The wavefront sensor 215 is also connected to an adaptive optic control unit 216, and informs the adaptive optic control unit 216 of the received wavefront. The wavefront correcting device 208 also is connected to the adaptive optic control unit 216, and performs modulation instructed by the adaptive optic control unit 216. The adaptive optic control unit 216 calculates a modulation amount (correction amount) for correction to a wavefront without aberration, based on the wavefront acquired from the measurement results by the wavefront sensor 215, and instructs the wavefront correcting device 208 to perform such modulation. Note that wavefront measurement and instruction to the wavefront correcting device 208 is performed repeatedly, with feedback control being performed to constantly have an optimal wavefront.

Part of the reflected/scattered light that has been transmitted through the light splitting unit 206 is reflected by the light splitting unit 204, passes through a collimator 212 and optic fiber 213 and is guided to a light intensity sensor 214. The light is converted into electric signals at the light intensity sensor 214, formed into an image serving as an eye image by a control unit 217, and displayed on a display 218. By increasing the oscillation angle of the scanning optical system in the configuration illustrated in FIG. 3 and the adaptive optic control unit 216 instructing not to perform aberration correction, the SLO image imaging apparatus 20 can also operate as a normal SLO apparatus, and can take wide-angle SLO images (wide-angle image D1).

Hardware Configuration and Execution Procedures of Image Processing Apparatus 10

Next, the hardware configuration of the image processing apparatus 10 will be described with reference to FIG. 4. In FIG. 4, 301 denotes a central processing unit (CPU), 302 memory (random access memory (RAM)), 303 control memory (read-only memory (ROM)), 304 an external storage device, 305 a monitor, 306 a keyboard, 307 a mouse, and 308 an interface. Control programs for realizing the image processing functions according to the present embodiment, and data used at the time of the control programs being executed, are stored in the external storage device 304. The control programs and data are loaded to the RAM 302 via a bus 309 as appropriate under control of the CPU 301, executed by the CPU 301, and function as the units described below. The functions of the blocks making up the image processing apparatus 10 will be correlated with specific execution procedures of the image processing apparatus 10 illustrated in the flowchart in FIG. 5.

Step 510: Image Acquisition

The image acquiring unit 111 requests the SLO image imaging apparatus 20 to acquire wide-angle images D1, high-magnification images Dhj, and corresponding fixation target positions F1 and Fh. In the present embodiment, the fixation target positions F1 and Fh are set at the fovea of the macula, and wide-angle images D1 and high-magnification images Dhj are acquired. Note that the setting method for shooting positions is not restricted to this, and may be set to any position.

The SLO image imaging apparatus 20 acquires and transmits the wide-angle images D1 and high-magnification images Dhj, and the corresponding fixation target positions F1 and Fh, in accordance with the acquisition request. The image acquiring unit 111 receives the wide-angle images D1, high-magnification images Dhj, and fixation target positions F1 and Fh, from the SLO image imaging apparatus 20 via the LAN 30, and stores these in the storage unit 120. Note that the wide-angle image D1 and high-magnification image Dhj in the present embodiment are moving images of which the inter-frame positioning has already been performed.

Step 520: Positioning

The positioning unit 131 performs positioning of the wide-angle images D1 and the high-magnification images Dhj, and obtains the relative position of the high-magnification images Dhj upon the wide-angle image D1. In a case where there is an overlapping region among the high-magnification images Dhj, the inter-image similarity is calculated regarding this overlapping region as well, and positions the high-magnification images Dhj with each other at the position where the inter-image similarity is the greatest.

Next, in a case where images of different magnification have been acquired in S510, positioning is performed from lower magnification images. For example, in a case where a high-magnification image D1*j* and a mid-magnification image D2*k* have been acquired, first, positioning is performed between the wide-angle image D1 and the mid-magnification image D2*k*, and next position is performed between the mid-magnification image D2*k* and the high-magnification image D1*j*. In a case where there are only high-magnification images, it is needless to say that positioning is performed only between the wide-angle image D1 and the high-magnification image D1*j*.

Note that the positioning unit 131 acquires the fixation target position Fh used for shooting the high-magnification image Dhj from the storage unit 120, and uses this to set a search start point for a positioning parameter in the positioning between the wide-angle image D1 and the high-magnification image Dhj. Any known technique can be used for inter-image similarity or coordinate conversion techniques. In the present embodiment, a correlation coefficient is used for inter-image similarity, and Affine transform is used as the coordinate conversion technique to perform positioning.

Step 530: Processing to Determine Suitability of Each Moving Image

The individual image determining unit 132 performs determination processing for suitability, based on the luminance values of the frames and the inter-frame movement amount. Further, the selecting unit 134 performs selection processing based on the suitability determination results, and forms individual images. An individual image here may be an image where all frames of the moving image have been overlaid, or may be one selected frame. An image where multiple images with relatively small noise and so forth are selected and the selected images are overlaid may be used. The processing of this step will be described in detail later with reference to the flowchart in FIG. 7A.

Step 540: Processing to Determine Suitability as Image Group

Based on the individual images formed in S530, the image group determining unit 133 determines suitability of an image group (multiple images of adjacent different positions) based on relative position and relative luminance therebetween, the selecting unit 134 selects a composition of images with the highest suitability, and composites these to form an image. In the present embodiment, the selecting unit 134 selects a frame interval of the composition regarding which the image group determining unit 133 has determined that the suitability is the highest at each acquiring position, performs overlaying to generate an image, and forms a composited image. The processing of this step will be described in detail later with reference to the flowchart in FIG. 7B.

Step 550: Display

The display control unit 135 displays the high-magnification images Dhj upon the wide-angle image D1, based on the value of a positioning parameter obtained in S520, or on the region, frame, or image selected in S540. The display control unit 135 may correct difference in concentration among high-magnification images for display, in a case where multiple high-magnification images Dhj have been acquired. Any known luminance correction method may be used. In the present embodiment, a histogram Hj is generated for each high-magnification image Dhj, and linear transform of the luminance values of the high-magnification images Dhj is performed so that the average and variance of the histograms Hj are common values among the high-magnification images Dhj, thereby correcting the difference in concentration. Note that the luminance correction method among high-magnification images is not restricted to this, and any known luminance correction method may be used. Further, with regard to the display magnification, a high-magnification image which the operator has specified via the instruction acquiring unit 140 is enlarged and displayed on the monitor 305.

Step 560: Instruction of Whether or not to Save Results

The instruction acquiring unit 140 externally acquires an instruction regarding whether or not to save to the data server 40 the wide-angle images D1, the high-magnification images Dhj selected by the selecting unit 134, the fixation target positions F1 and Fh, and the positioning parameter values acquired in S520. This instruction is input by the operator from the keyboard 306 or mouse 307, for example. In a case where saving has been instructed, the flow advances to S570, and in a case where saving has not been instructed, the flow advances to S580.

Step 570: Saving Results

The image processing unit 130 correlates the date and time of the examination, information identifying the examined eye, the wide-angle images D1, the high-magnification images Dhj selected by the selecting unit 134 and the fixation target positions F1 and Fh, and the positioning parameter values, and transmits to the data server 40.

Step 580: Instruction of Whether or not to End Processing

The instruction acquiring unit 140 externally acquires an instruction regarding whether or not to end processing by the image processing apparatus 10 regarding the wide-angle images D1 and high-magnification images Dhj. This instruction is input by the operator from the keyboard 306 or mouse 307, for example. In a case where an instruction to end processing has been acquired, the processing ends. On the other hand, in a case where an instruction to continue the processing has been acquired, the flow returns to S510, and processing is performed on the next eye to be examined (or processing is performed again regarding the same eye for examination).

Processing Regarding Determination of Suitability for Each Moving Image

Figure 7A:
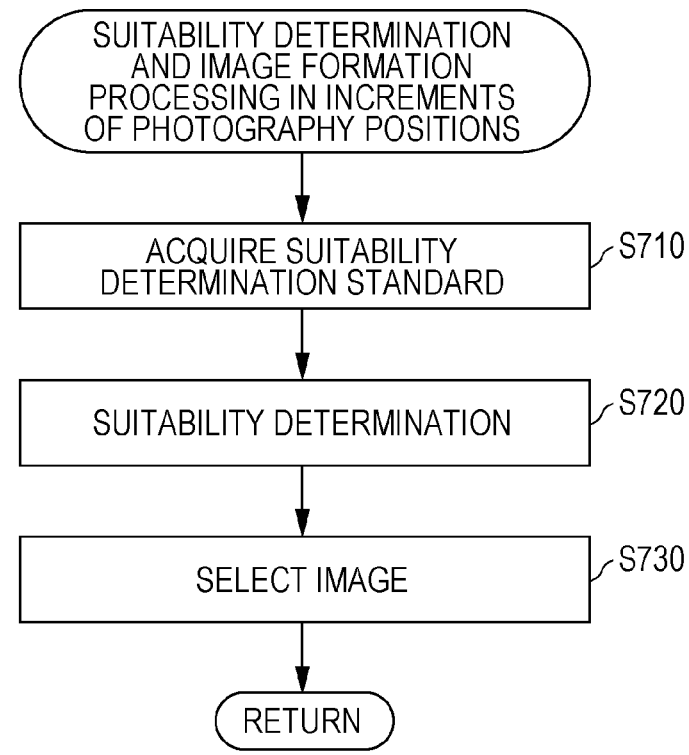
FIGS. 7A and 7B are flowcharts illustrating the details of processing executed in S530 and S540 according to the first embodiment of the present invention.

Next, processing executed in S530 will be described in detail with reference to the flowchart in FIG. 7A.

Step 710: Acquisition of Suitability Determination Standard

The individual image determining unit 132 acquires a suitability determination standard via the instruction acquiring unit 140. The following items a) through d) are listed here as suitability determination standards;

a) that the luminance value of the image is in an appropriate range, b) range of appropriate values of image quality (S/N ratio, etc.), c) that the amount of movement as to the reference frame is in an appropriate range, and d) that the focus position is in an appropriate range, where, a) is acquired as the suitability in the present embodiment. This is to exclude low-luminance frames which occur due to measurement light not reaching the fundus, as a result of blinking or marked deviation of fixation position.

Step 720: Suitability Determination

The individual image determining unit 132 determines suitability for each frame of the high-magnification SLO image Dhj, following the standard acquired in S710. In the present embodiment a value of 1 is assigned if each a) is in an appropriate range, and a value of −1 is assigned if out of an appropriate range.

Step 730: Image Selection

The selecting unit 134 selects images (frames in a case of moving images) to use for display, in increments of shooting positions, based on the suitability determined in S720, and forms an image. In the present embodiment, a high-magnification image is a moving image where photoreceptors have been imaged as illustrated in FIG. 6C, and an overlaid image is formed from the moving image. The following items (i) and (ii) can be listed as principles for forming individual images here, which is to (i) maximize the number overlaid (priority given to image quality), and (ii) maximize area of overlaid image (priority given to prevention of incomplete images).

In the case of (i), all frames selected in S720 are used for overlaying. For example, in a case where the position of each frame in an individual high-magnification moving image is correlated (Nf: frame No.) as illustrated in FIG. 6(c), the results of overlaying are as illustrated in FIG. 6D. In this example, the leading frame is the reference frame. Regions not used for overlaying (incomplete images) are indicated by black in FIG. 6D. While high quality images, regions with frames having no pixel values as a result of inter-frame positioning are not used in the overlaying, so incomplete images readily occur. In the case of (ii), frames selected in S720 which have even slight positional deviation are excluded. For example, in the case of FIG. 6C, frames Nos. 2 through 4 are excluded. While incomplete images do not occur, the number of images overlaid is smaller, so the image quality tends to be lower than in the case of (i). Now, in the case of the present embodiment, frames with suitability of 1 calculated in S720 are selected, and an overlaid image is formed following the principle (i), which is to say that only regions where the pixel values are positive in all selected frames are used.

Processing to Determine Suitability as Image Group

Figure 7B:
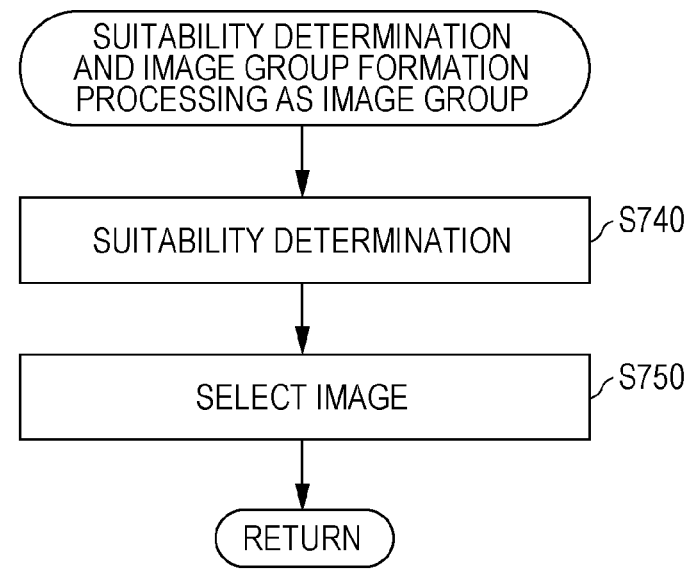

Next, the processing executed in S540 will be described in detail with reference to the flowchart in FIG. 7B.

Step 740: Suitability Determination

The image group determining unit 133 composites the image group formed in S730 following the positioning parameter used in S520, and determines suitability of the image group based on the relative position and luminance properties of the image group. Assumption will be made in the present embodiment that the image group is made up of nine overlaid images such as illustrated in FIG. 6G, and that the image No. j increases in raster scanning (zigzag scanning) order from the upper left. Determination principles relating to suitability of the composited images (image group) are as listed below in order of priority, which is to say, 1. that no incomplete-image region is generated in the composited image, 2. that the image quality does not vary according to the shooting position, and 3. that as many images as possible are overlaid.

Of these, 1 and 2 are conditions set for enabling within the composited image to be observed under the same conditions, with the position determining unit 1331 determining condition 1, and the luminance determining unit 1332 determining condition 2. Both of the relative position and luminance properties of the image group do not have to be set as conditions; setting either one as a condition is sufficient.

Now, in a case where suitability as an image group is not determined, i.e., in a case where the composited image is generated following the principle of (ii) in S730 for each shooting position, there will be cases where the above condition 2 is not satisfied. Also, in a case where the composited image is generated following the principle of (ii) such that the above condition 2 is satisfied, the image quality is lower than a case where suitability of the image group is determined and images are selected, since the number of overlaid images has to match that of the image with the fewest overlaid images. Accordingly, performing suitability determination taking into consideration data continuity and complementation at the edges and overlapping portions of adjacent images enables a higher-quality composited image to be obtained (overlaying being performed with a greater number of images), while satisfying conditions 1 and 2.

In the present embodiment, there are redundant regions between two adjacent images, such as indicated by the gray regions in FIG. 6F, and redundant regions between four adjacent images, such as indicated by the black regions in FIG. 6F. Specifically, the suitability of the image group is determined by the following procedures.

(1) Individual images generated in S730 (priority on image quality) are composited according to the positioning parameters obtained in S520.

(2) Whether or not there are incomplete images within the composited image generated in (1) is checked, and (area of composited image−area of incomplete images)/(area of composited image)

is calculated.

Step 750: Image Selection

The selecting unit 134 performs image selection in each high-magnification image so that the suitability is the highest, based on the suitability determined in S740, and performs formation processing of the image group based on the selected images. Specifically, image selection (selection of frame or region) is performed according to the following procedures, and image group formation processing is performed.

(3) If there are no incomplete images, the composited image is formed as it is and the processing ends.

(4) If there are incomplete images, the position of the incomplete-image region is obtained.

(5) Check whether or not there is complementary (substitute) data in a redundant region of an image including the incomplete-image region or having a side adjacent to the incomplete-image region. For example, in FIG. 6G there are incomplete images in image 6 and image 9, so whether or not there is complementary data at image 6 and the left edge of image 5, and in image 9, is checked.

(6) If there is complementary (substitute) data, the incomplete image region is replaced with complementary data that has the best image quality (the number of overlaid images is the greatest) of the complementary data, and (8) is executed (equivalent to region selection processing in the image by the selecting unit 134).

(7) If there is no complementary (substitute) data, selected frames of images having images including incomplete-image regions or a side adjacent to the region are changed so that the incomplete-image region is resolved. If there are multiple frame selection methods to resolve the incomplete-image region, the frame selection method where the number of overlaid images is the greatest is selected.

(8) The number of overlaid images ANmin that is the smallest number of overlaid images out of the overlaid image group obtained in (7) is set as the number of overlaid images of the composited image, the number of overlaid images at each shooting position is changed to ANmin, and the overlaid image is generated again.

(9) The overlaid image generated in (8) is used to generate a composited image. There are no more incomplete images, as illustrated in FIG. 6H, and a composited image where the numbers of overlaid images are the same and are maximal is generated.

Note that in a case where moving images have been acquired Nt times (Nt≥2) at the same shooting position in the same examination, the moving image with the highest suitability (of the first through Nt'th times) is selected in S730, whether or not there is substitute data regarding the incomplete-image region in a different shooting time is checked in image selection (5) in S750, and substitution is made with the substitution data having the highest image quality of all substitution data. If there still is an incomplete-image region remaining, whether or not there is substitution data in a redundant region of an adjacent image may be checked.

Note that while the composited image formed based on the determination of suitability as an image group has been described as being a still image (overlaid image) in the present embodiment, the present invention is not restricted to this. For example, suitability determination may be performed taking into consideration complementation of data at the edges and overlapping portions of adjacent moving images, and a moving image may be composited and displayed thereupon, as illustrated in FIG. 6J.

The flow of the basic processing in a case of composited display of moving images is the same as in a case of composited display of still images, but the following points differ as follows.

(i) A time phase data acquiring apparatus 50 such as illustrated in FIG. 2B is connected to the image processing apparatus 10, and time phase data is acquired simultaneously with the moving image. Time phase data is biosignal data acquired by a sphygmograph, for example. Referencing the time phase data yields the cardiac cycle of each moving image, i.e., which cycle should be played. The playback cycle is aligned to be the same among the moving images by frame interpolation processing of the moving images.

(ii) The longest continuous frame section from which frames with abnormal luminesce have been removed is selected in the image formation processing in increments of shooting position in S730.

(iii) Suitability determination is performed in the suitability determination processing as an image group in S740 according to the following principles, which is to say that
 no incomplete-image regions generated in composited image,
 no variance in number of playback frames from one shooting position to another, and
 composite and display moving images of as many frames (cycles) as possible.

(iv) The frames selected in (6) (7) (8) of the image formation processing as an image group in S750 are set as a continuous frame section.

Accordingly, incomplete images are eliminated from the composited display of the moving image, and a composited moving image with the longest continuation of frames having the same number of playback frames is formed. In a case where no time phase data is acquired, a composited display may be made as a moving image without adjusting the playback clock time.

According to the configuration described above, when displaying a composited image of adaptive optic SLO images at different shooting positions, the image processing apparatus 10 determines suitability of an image group in a case of comparing with a region to be shot, i.e., determines suitability based on how small an unobservable region is. Regions or frames or images are selected from images based on data continuity and complementation at edges or overlapping regions of adjacent images, so that the suitability is greatest, and composited and displayed. Accordingly, in a case where cells and tissue to be observed, and lesions thereof, exist across multiple high-magnification images, a composited image which can be observed under generally the same conditions can be generated.

Second Embodiment

Continuity of Image Features of Multiple Images at Different Positions

An image processing apparatus according to a second embodiment is configured to determining suitability of an image group based on the continuity of image features extracted from adjacent high-magnification images, rather than determining suitability of an image group based on continuity of relative position and luminance properties of adjacent high-magnification images as in the first embodiment. Specifically, the suitability of an image group is determined based on the continuity of capillary regions of the parafovea extracted from high-magnification SLO images.

Figure 8:
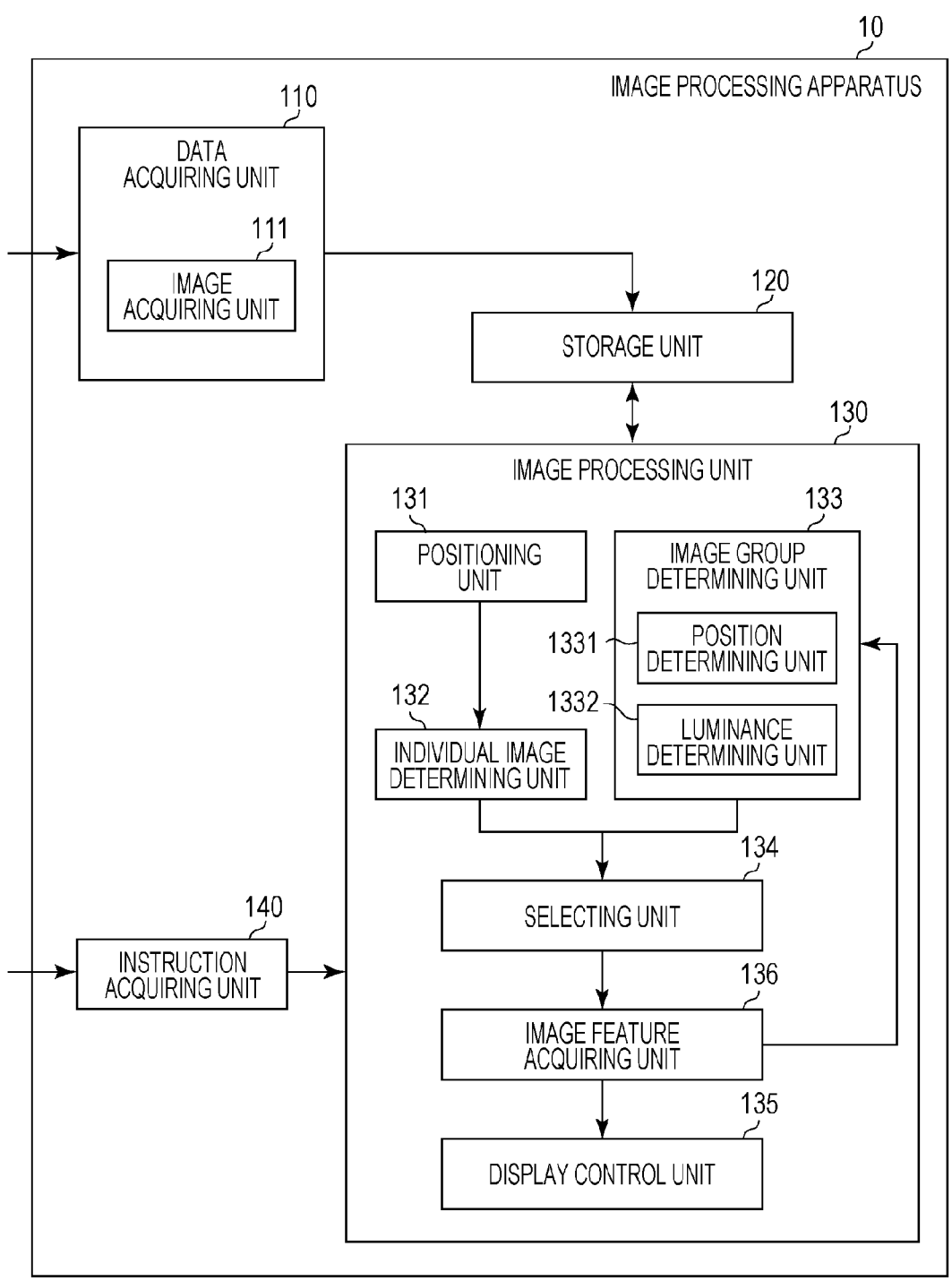
FIG. 8 is a block diagram illustrating a functional configuration example of an image processing apparatus according to a second embodiment of the present invention.

The configuration of apparatuses connected with the image processing apparatus 10 according to the present embodiment is the same as in the first embodiment. The data server 40 holds, besides the wide-angle images D1 and high-magnification images Dh of the inspected eye, and acquisition conditions such as fixation target positions F1 and Fh used for the acquisition thereof, image features of the eye and normal values relating to distribution of the image features of the eye. While any image features of the eye can be held, image features relating to the retinal blood vessels, capillaries Q, and blood cells W, are used in the present embodiment. Image features of the eye output from the image processing apparatus 10 are saved in the data server 40. Also, image features of the eye and normal value data relating to distribution of image features of the eye are transmitted to the image processing apparatus 10 upon request from the image processing apparatus 10. FIG. 8 illustrates functional blocks of the image processing apparatus 10 according to the present embodiment. This differs from the case in the first embodiment with regard to the point that the image processing unit 130 is provided with an image feature acquiring unit 136. The image processing flow according to the present embodiment is the same as that in FIG. 5, with S510, S520, S560, S570, and S580 being the same as in the first embodiment. Accordingly, only the processing of S530, S540, and S550 will be described in the present embodiment.

Step 530: Processing to Determine Suitability of Each Moving Image

The individual image determining unit 132 performs determination processing for suitability, based on the luminance values of the frames and the inter-frame movement amount. Further, the selecting unit 134 performs selection processing based on the suitability determination results, and forms individual images. The processing of this step will be described in detail later with reference to the flowchart in FIG. 10A.

Step 540: Processing to Determine Suitability as Image Group

Based on the individual images formed in S530, the image group determining unit 133 determines suitability based on continuity of image features between images, the selecting unit 134 selects a composition of images with the highest suitability, and composites these to form an image. The processing of this step will be described in detail later with reference to the flowchart in FIG. 10B.

Step 550: Display

Figure 9B:
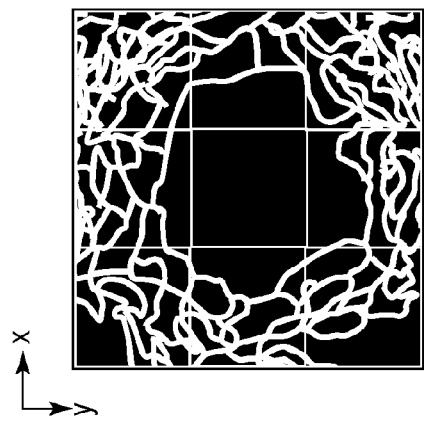
FIGS. 9A through 9E are diagrams illustrating what is performed in image processing according to the second embodiment of the present invention.

The display control unit 135 displays the composited image formed in S540 using the positioning parameters obtained in S520. Display of composited images where capillaries such as illustrated in FIG. 9B have been extracted is performed in the present embodiment.

Processing to Determine Suitability for Each Moving Image

Figure 10A:
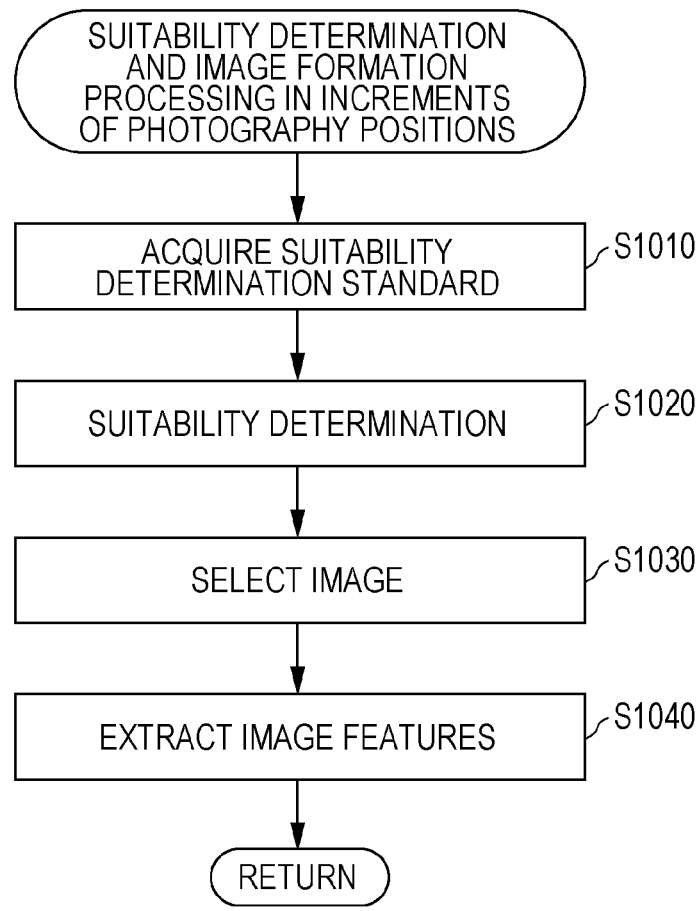
FIGS. 10A and 10B are flowchart illustrating the details of processing executed in S530 and S540 according to the second embodiment of the present invention.

Next, the processing executed in S530 will be described in detail with reference to the flowchart illustrated in FIG. 10A. Note that S1010 and S1020 are the same as S710 and S720 in the first embodiment, so description thereof will be omitted.

Step 1030: Image Selection

The selecting unit 134 selects images (frames in a case of moving images) to use for display, in increments of shooting positions, based on the suitability determined in S1020, and forms an image. In the present embodiment, a high-magnification image is a moving image where a capillary region has been imaged, and an image where capillaries have been extracted from the moving image (hereinafter written as "capillary image") is formed.

The following items (i) and (ii) can be listed as principles for forming individual images, which is to say, (i) maximize the number of frames used to form the capillary image (priority given to image quality), and (ii) maximize area of capillary region (priority given to prevention of incomplete images).

In the case of (i), all frames selected in S1020 are used to extract capillaries. In the case of (ii), frames selected in S1020 which have even slight positional deviation are excluded. For example, in the case of FIG. 6C, frames Nos. 2 through 4 are excluded. While incomplete images do not occur, the number of frames used to extract capillaries is smaller, so the image quality tends to be lower than in the case of (i). Now, in the case of the present embodiment, frames with suitability of 1 calculated in S1020 are selected, and capillary regions are extracted following the principle (i), which is to say that only regions where the pixel values are positive in all selected frames are used.

Step 1040: Extracting Image Features

The image feature acquiring unit 136 detects capillaries from high-magnification images Dhj, and detects the avascular area boundary from the detected capillary regions. In the present embodiment, first capillaries are identified from the high-magnification images Dhj as blood cell component movement ranges, according to the following procedures, which is to say that (a) difference processing is performed among adjacent frames of high-magnification images Dhj regarding which inter-frame positions has been completed (a difference moving image is generated), (b) luminance statistics (variance) in the frame direction are calculated at each x-y position of the difference moving image generated in (a), and (c) a region where luminance variance each x-y position of the difference moving image exceeding a threshold value Tv is identified as being a region where blood cells have moved, i.e., a capillary region.

Note that the method for detecting capillaries is not restricted to this; any known method may be used. For example, blood vessels may be detecting by applying a filter that enhances linear structures to a particular frame of the high-magnification images Dhj.

Next, the image feature acquiring unit 136 detects the avascular area boundary from the acquired capillary regions. There is a region where no retinal blood vessels exist (avascular area) near the fovea of the retina (e.g., Dh5 in FIG. 6I). Early-stage lesions of retinal blood vessels readily occur around the avascular area boundary, and also the avascular area spreads as lesions such as retinopathy of diabetes advance. Accordingly, the avascular area boundary is an important object of observation and analysis.

In the present embodiment, a circular deformable model is placed in the high-magnification image Dh5 situated at the center of the high-magnification image group, and this deformable model is deformed so as to match the avascular area boundary, thereby identifying the avascular area boundary. The position of the deformable mode regarding which deformation has been completed is taken as a candidate position of the avascular area boundary. Note that the method for identifying the avascular area boundary is not restricted to this; any known technique may be used.

Processing to Determine Suitability as Image Group

Figure 10B:
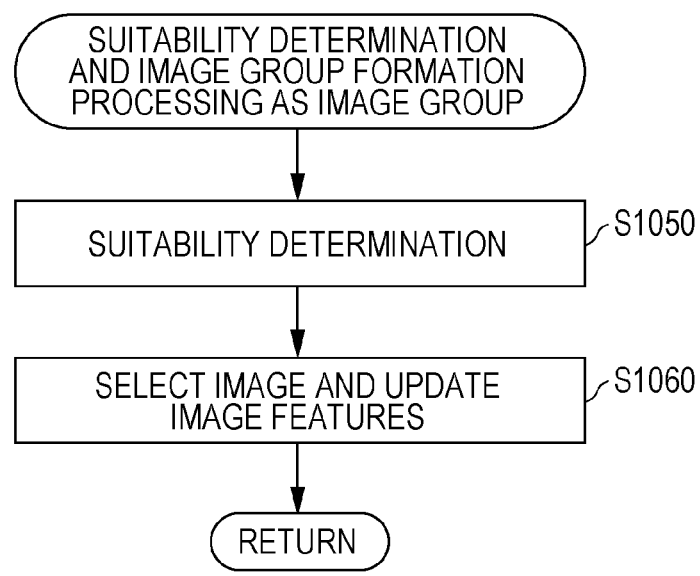

Next, the processing executed in S540 will be described in detail with reference to the flowchart in FIG. 10B.

Step 1050: Suitability Determination

The image group determining unit 133 calculates the following index relating to the image features (capillary area) acquired from the high-magnification images Dhj, and determines suitability of the image group based on this index.

(Sum of length of avascular area boundary actually acquired)/(Sum of length of avascular area boundary candidate point sequence set in S1040)

Step 1060: Image Selection and Updating Image Features

The selecting unit 134 selects images in the high-magnification images so that the suitability is the greatest, based on the suitability determined in S1050, and performs forming processing of the image group based on the selected images. Specifically, image selection is performed according to the following procedures, and image group formation processing is performed.

(3') If there are no incomplete image features, the composited image is formed as it is and the processing ends.

(4') If there are incomplete image features, the position of the incomplete-image-feature region is obtained.

Figure 9A:
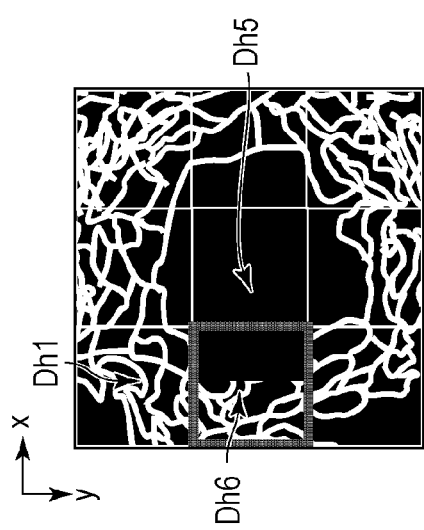

(5') Check whether or not there is complementary (substitute) data in a redundant region of an image including the incomplete-image-feature region or having a side adjacent to the incomplete-image-feature region. For example, in FIG. 9A there are incomplete image features in image 6, so whether or not there is complementary data at image 6 and the left edge of image 5 is checked.

(6') In a case where there is complementary (substitute) data, the incomplete-image-feature region is replaced by complementary data that has the best image quality of the complementary data (the number of frames used for capillary extraction is great), and (8') is executed.

(7') If there is no complementary (substitute) data, selected frames of images having images including incomplete-image-feature regions or a side adjacent to the region are changed so that the incomplete-image-feature region is resolved. If there are multiple frame selection methods to resolve the incomplete-image-feature region, the frame selection method where the number of selected frames is the greatest is selected.

(8') The number of frames ANmin' used for generating the capillary image, that is the smallest number frames used for generating the capillary image, of the capillary image group obtained in (7'), is set as the number of frames used in each capillary image. The number of frames used for capillary extraction at each shooting position is changed to ANmin', and the capillary image is generated again.

(9') The capillary image generated in (8') is used to generate a composited image. There are no more incomplete image features, as illustrated in FIG. 6H, and a composited image where the numbers of frames used for capillary extraction are the same and are maximal is generated.

Figure 9E:
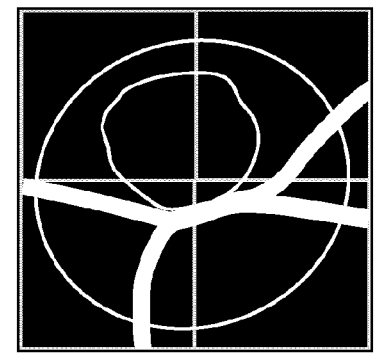
Figure 9D:
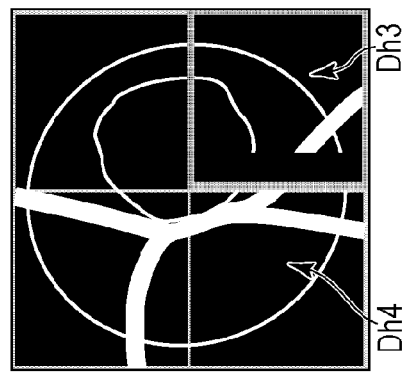
Figure 9C:
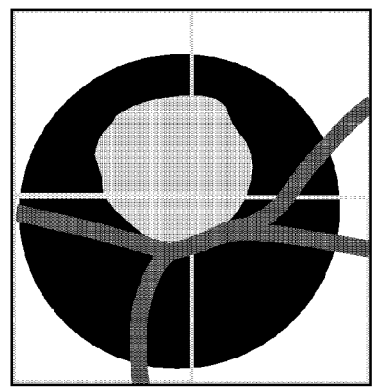

Note that the image features used to calculate the suitability for the image group are not restricted to the avascular area boundary; any image features may be used. For example, in a case of determining suitability of an image group of four high-magnification images taken of the optic papilla as illustrated in FIG. 9C, a cupped portion can be detected by threshold value processing, and the suitability of the image group determined based on the continuity of the boundary position of the cupped portion. Specifically, the sum of the edge of the cupped portion boundary is used as the suitability of the image group. Of course, the suitability of the image group is not restricted to this, and may be the area of the cupped region detected by threshold processing, for example.

The image selection method where the suitability of the image group is the greatest is basically the same as S750 in the first embodiment. This differs from the case of the first embodiment though, in that feature extraction (cupped portion boundary detection) is performed as to the overlaid image generated after frame selection, suitability for the image group is determined using the continuity of the image features, and the images subjected to feature extraction are composited. Due to this sort of suitability determination processing of the image group and image group forming processing, the composited image with discontinuous portions in image features like in the high-magnification image Dh3 at the lower right in FIG. 9D, can have the discontinuous portions resolved as in FIG. 9E and the tissue to be analyzed can be analyzed under generally the same conditions.

According to the configuration described above, the image processing apparatus 10 determines suitability of an image group based on continuity of image features extracted from adjacent high-magnification images. Accordingly, in a case where cells and tissue to be analyzed, and lesions thereof, exist across multiple high-magnification images, a composited image which can be analyzed under generally the same conditions can be generated. Note that in addition to image features, at least one condition of the relative position and luminance properties of the image group, which are conditions of the first embodiment, for example, may be added as a condition for determining the suitability of the image group.

Third Embodiment

Tomographic Image Imaging Apparatus Having Adaptive Optic System

When compositing and displaying high-magnification adaptive optic OCT tomography images taken at different shooting positions, the image processing apparatus according to a third embodiment determines the suitability of an image group based on how small an unobservable (unanalyzable) region is when compared with a shot (analyzed) region. Specifically, description will be made regarding a case of acquiring multiple (3×3×3=27) high-magnification images near the fovea and compositing by positioning processing, and determining the suitability of the image group based on how small an unobservable (unanalyzable) region is in comparison with a region to be imaged (analyzed).

FIG. 2C illustrates the configuration of devices connected to the image processing apparatus 10 according to the present embodiment. The present embodiment differs from the first embodiment with regard to the point that connection is made with the tomographic image imaging apparatus 60 having an adaptive optic system. The tomographic image imaging apparatus 60 is an apparatus that takes tomographic images of the eye, and is configured as a spectral domain optical coherence tomography (SD-OCT) apparatus. The eye tomographic image imaging apparatus 60 images three-dimensional images tomographic images of an eye to be examined, in response to operations by an operator omitted from illustration. The imaged tomographic images are transmitted to the image processing apparatus 10.

Next, the functional blocks of the image processing apparatus 10 according to the present embodiment are the same as those of the case of the first embodiment, so description will be omitted. The data server 40 holds normal value data relating to image features of the eye and distribution of image features of the eye, and in the present embodiment holds normal value data relating to the retina layer boundary and the shape and thickness thereof.

Figure 11:
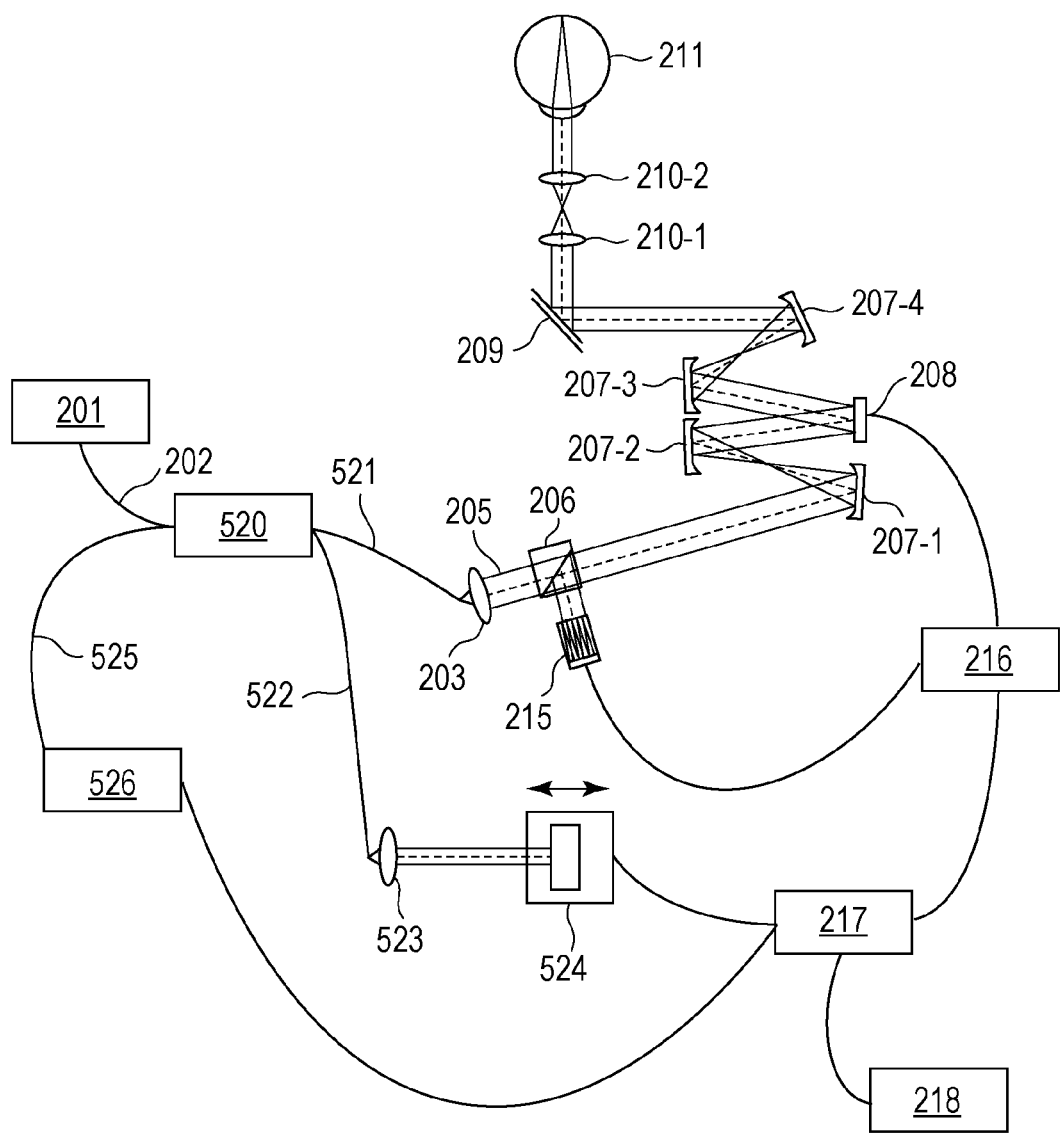
FIG. 11 is a diagram for describing the overall configuration of a tomographic image imaging apparatus according to a third embodiment of the present invention.

Next, the configuration of the tomographic image imaging apparatus 60 that has an adaptive optic system will be described with reference to FIG. 11. In FIG. 11, 201 denotes a light source, for which an SLD light source having a wavelength of 840 nm is used in the present embodiment. A low-interference arrangement is sufficient for the light source 201, and an SLD light source having a wavelength interval of 30 nm or longer is preferably used. Also, an ultrashort pulsed laser such as a Ti:sapphire laser may also be used as the light source. Light irradiated from the light source 201 passes through a single-mode optic fiber 202 and is guided to a fiber coupler 520. The fiber coupler 520 splits this light to a measurement light path 521 and a reference light path 522. A fiber coupler is used which has a splitting ratio of 10:90, so that 10% of the quantity of input light goes to the measurement light path 521. The light which has passed through the measurement light path 521 is irradiated as parallel measurement light from a collimator 203. The configuration downstream of the collimator 203 is the same as in the first embodiment, with the eye 211 being irradiate via the adaptive optic system and scanning optical system, and the reflected and scattered light from the eye 211 returns the same path to be guided to the optic fiber 521 and reaches the fiber coupler 520. On the other hand, the reference light which has passed through the reference light path 522 is emitted at a collimator 523, reflected at a variable optical path length unit 524, and returns to the fiber coupler 520 again. The measurement light which has reached the fiber coupler 520 is multiplexed with the reference light and passes through optical fiber 525 to be guided to a light splitting unit 526. A tomographic image of the eye is configured by the control unit 217 based on interference light information split by the light splitting unit 526. The control unit 217 can control the variable optical path length unit 524 to acquire an image of a desired depth position. Note that by increasing the oscillation angle of the scanning optical system in the configuration illustrated in FIG. 11 and the adaptive optic control unit 216 instructing not to perform aberration correction, the tomographic image imaging apparatus 60 can operate as a normal tomographic image imaging apparatus, and can take wide-angle tomographic images (wide-angle image D1).

Also, while the tomographic image imaging apparatus 60 having the adaptive optic system is described as being an SD-OCT in the present embodiment, SD-OCT is not essential. For example, this may be configured as a time-domain OCT or an SS-OCT (Swept Source Optical Coherence Tomography). In the case of SS-OCT, a light source is used where lights of different wavelengths are generated at different times, and spectral elements to acquire spectral information become unnecessary. Also, an SS-OCT can acquire very deep images including not only the retina but also the chorioid.

FIG. 5 illustrates the image processing flow of the image processing apparatus 10 according to the present embodiment. This the same as the case in the first embodiment except for S510, S520, S530, S540, and S550, so only the processing of S510, S520, S530, S540, and S550 will be described.

Step 510: Image Acquisition

The image acquiring unit 111 requests the image imaging apparatus 60 to acquire wide-angle images D1, high-magnification images Dhj, and corresponding fixation target positions F1 and Fh. In the present embodiment, the fixation target positions F1 and Fh are set at the fovea of the macula, and wide-angle images D1 and high-magnification images Dhj are acquired. The high-magnification images Dhj are repeatedly taken Np times (Np=3 in the present embodiment) and a high-magnification image taken at the n'th time at the same shooting position is written as Dhj_n in the present embodiment, for example. Note that the setting method for shooting positions is not restricted to this, and may be set to any position.

The tomographic image imaging apparatus 60 acquires and transmits the wide-angle images D1 and high-magnification images Dhj_n, and the corresponding fixation target positions F1 and Fh, in accordance with the acquisition request. The image acquiring unit 111 receives the wide-angle images D1, high-magnification images Dhj_n, and fixation target positions F1 and Fh, from the tomographic image imaging apparatus 60 via the LAN 30, and stores these in the storage unit 120. Note that the wide-angle image D1 and high-magnification image Dhj_n in the present embodiment are three-dimensional images regarding which inter-slice positioning has already been performed.

Step 520: Positioning

The positioning unit 131 performs positioning of the wide-angle images D1 and the high-magnification images Dhj_n, and decides the position of the high-magnification images Dhj_n upon the wide-angle image D1. First, the image group determining unit 133 acquires the fixation target position Fh used when shooting the high-magnification image Dhj_n from the storage unit 120, and sets a search start point for a positioning parameter for the positioning of the wide-angle image D1 and high-magnification images Dhj_n, based on the relative position from the fixation target position. In a case where there is an overlapping region among the high-magnification images Dhj_n, the inter-image similarity is calculated regarding this overlapping region as well, and the high-magnification images Dhj_n are positioned with each other at the position where the inter-image similarity is the greatest.

Next, in a case where images of different magnification have been acquired in S530, positioning is performed from lower magnification images. In the present embodiment, there are only high-magnification images, so positioning is performed only between the wide-angle image D1 and the high-magnification images D1j_n. Any known technique can be used for inter-image similarity or coordinate conversion techniques, and in the present embodiment, a (three-dimensional) correlation coefficient is used for inter-image similarity, and three-dimensional Affine transform is used as the coordinate conversion technique to perform positioning.

Step 530: Processing to Determine Suitability of Each Moving Image

Figure 12A:
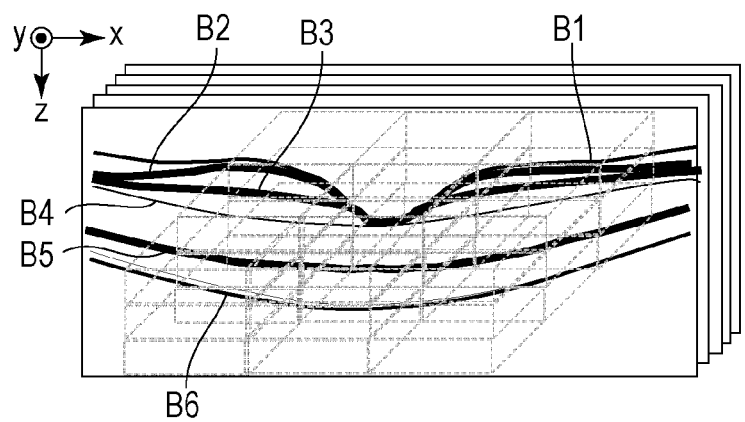
FIGS. 12A through 12D are diagrams illustrating what is performed in image processing according to the third embodiment of the present invention.

The individual image determining unit 132 performs determination processing for suitability, based on the luminance values of the frames and the inter-frame movement amount. Further, the selecting unit 134 performs selection processing based on the suitability determination results, and forms individual images. The determination standard acquisition and similarity determination method are the same as S710 and S720 in the first embodiment, so description will be omitted here. Next, the selecting unit 134 selects images to be used for display in increments of shooting positions, based on the determined similarity, and forms an image. The high-magnification images in the present embodiment are three-dimensional tomographic images such as illustrated in FIG. 12(a). Overlapping among high-magnification images is omitted in the illustration here, to facilitate comprehension of the shooting position.

The following can be conceived as individual image forming principles, which is to (i) maximize the S/N ratio (priority given to image quality), and (ii) maximize total number of pixels in three-dimensional tomographic image (priority given to prevention of incomplete images),
in which, with regard to (i), of the tomographic images acquired at the same shooting position in S510, the image with the highest S/N ratio is selected, and the pixel value for a region including a slice with no pixel value (image edge portion) is set to 0. The image quality is high, but incomplete images readily occur. With regard to (ii), the three-dimensional tomographic image regarding which the processing of filling the image edges with zeros is the smallest is selected from the three-dimensional tomographic images (a total of three) acquired in S510. While incomplete images do not occur, the S/N ratio is not necessarily high, so the image quality tends to be lower than in the case of (i). In the present embodiment, a slice of which the suitability 1 is selected, and the luminance value in a slice of which the suitability is −1 is a value obtained by interpolation processing by pixel values in preceding and following slices. Here, high-image quality individual images are formed following the principle (i), i.e., using the three-dimensional tomographic image of which the S/N ratio is the greatest.

Step 540: Processing to Determine Suitability as Image Group

Based on the individual images formed in S530, the image group determining unit 133 determines suitability of an image group, and the selecting unit 134 selects a composition of images with the highest suitability and composites these to form an image. In the present embodiment, the image No. j increases in raster scanning (zigzag scanning) order from the upper left. Determination principles relating to the composited images (image group) are as listed below in order of priority, which is to say 1. that no incomplete-image region is generated in the composited image, and 2. that the composited image is as high quality as possible.

Of these, 1 is a condition set for enabling within the composited image to be observed under the same conditions. Now, in a case where suitability as an image group is not determined, frames need to be selected so that there are no incomplete image regions at each shooting position for example, a composited image with lower image quality is formed in relation with condition 2 described above, as compared to a case of generating a composited image based on suitability determination of the image group. Accordingly, performing suitability determination taking into consideration data continuity and complementation at the edges and overlapping portions of adjacent three-dimensional tomographic images enables a higher-quality composited image to be obtained, while satisfying condition 1.

Figure 12B:
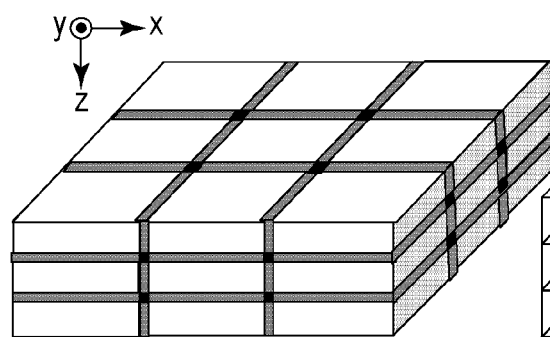
Figure 12C:
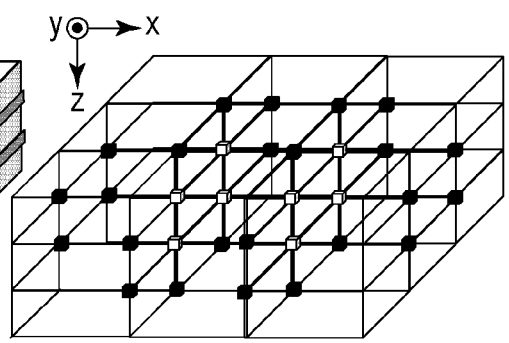

In the present embodiment, there are redundant regions among two adjacent images as indicated by the gray regions in FIG. 12B, redundant regions among four adjacent images as indicated by the black regions in FIG. 12B, and redundant regions among eight adjacent images as indicated by the white grid points in FIG. 12C. Specifically, the suitability of the image group is determined by the following procedures.

(1) Individual images generated in S530 (priority on image quality) are composited according to the positioning parameters obtained in S520.

(2) Whether or not there are incomplete images within the composited image generated in (1) is checked, and (volume (number of pixels) of composited three-dimensional image−volume (number of pixels) of incomplete images)/(volume (number of pixels) of composited three-dimensional image)

is calculated as the suitability of the image group.

Note that image group suitability is not restricted to this, and that projection images of individual images may be composited upon a projected image of a wide-angle image based on the positioning parameters obtained in S520, and (area of composited two-dimensional image−area of incomplete images)/(area of composited two-dimensional image)

may be determined.

Based on the suitability of the image group determined above, the selecting unit 134 performs image selection so that the suitability is the highest at each shooting position, and an image group is formed based on the selected image. Specifically, image selection is performed according to the following procedures, and image group formation processing is performed.

(3) If there are no incomplete images, the composited image is formed as it is and the processing ends.

(4) If there are incomplete images, the position of the incomplete-image region is obtained.

Figure 12D:
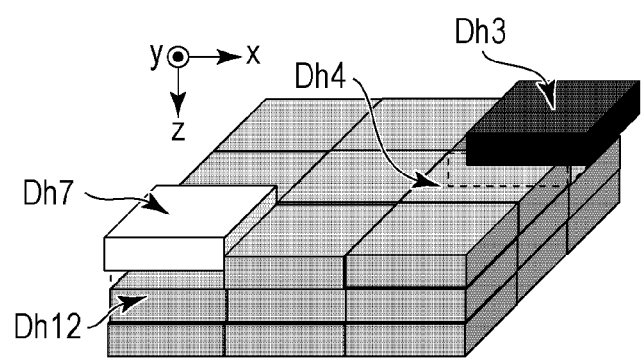

(5) Check whether or not there is substitute data in a redundant region of an image including the incomplete-image region or having a side adjacent to the incomplete-image region. For example, in FIG. 12D there are incomplete images in high-magnification images Dh3 and Dh7, so whether or not there is complementary (substitute) data at Dh3 and the far edge of Dh4, and Dh7 and the upper edge of Dh12, is checked.

(6) If there is complementary (substitute) data, the incomplete image region is replaced with complementary data that has the best image quality (the highest S/N ratio) of the complementary data, and image compositing processing is performed.

(7) If there is no complementary (substitute) data, trimming processing (filling in with zeros) at the edge of the image is cancelled so that the incomplete-image region is the smallest, pixel values are decided for the remaining incomplete-image region by interpolation processing from nearby pixels, and then image compositing processing is performed. Thus, a composited image where there are no incomplete images and the image quality is the highest, is formed. Note that the image group suitability determination principles are not restricted to the above-described, and that any suitability may be set. For example, the length of the avascular area boundary, which is an example of image features, may be added to the conditions for suitability besides area and so forth.

Step 550: Display

The image group determining unit 133 the composited image formed in S540 on the monitor 305. The wide-angle image D1 and high-magnification images Dhj_n are both three-dimensional tomographic images in the present embodiment, so the two following types of display are performed.

i) Projection images of the wide-angle image D1 and high-magnification images Dhj_n are generated with regard to the z-axial direction, and a projected image of a high-magnification image Dhj_n is composited and displayed on a projected image of the wide-angle image D1.

ii) A wide-angle three-dimensional tomographic image D1" is generated, displayed according to the pixel values of a wide-angle three-dimensional tomographic image D1 at positions where only the wide-angle three-dimensional tomographic image D1 has been acquired, and according to pixels values of the high-magnification three-dimensional tomographic image Dhj_n at positions where both the wide-angle three-dimensional tomographic image D1 and the high-magnification three-dimensional tomographic image Dhj_n have been acquired. Further, a particular scanning position on the wide-angle three-dimensional tomographic image D1" is indicated on the superimposed image in i) by an arrow, and a two-dimensional tomographic image of the wide-angle three-dimensional tomographic image D1" defined by the position of the arrow is displayed along with a superimposed image such as in i). In this display, not only a two-dimensional tomographic image of the wide-angle three-dimensional tomographic image D1, but also a two-dimensional tomographic image of the high-magnification three-dimensional tomographic image Dhj_n is displayed superimposed.

Further, in the display of ii), the arrow indicating the display position of the wide-angle tomographic image D1" can be (vertically or horizontally) moved by the operator using the instruction acquiring unit 140, so the displayed slice of the wide-angle image D1 and high-magnification image Dhj_n defined (displayed) along with this operation also changes.

Note that the method of generating the projected images is not restricted to mean intensity projection; any projection method may be used. Also, the high-magnification images Dhj_n are not restricted to still images, and may be moving images. Although suitability of a tomographic image group has been described in the present embodiment as being determined based on how small an unobservable region is as to the region of shooting, the present invention is not restricted to this. An arrangement may be made where, the same as with the case of the second embodiment, the image processing apparatus 10 has the image feature acquiring unit 136, and suitability of a tomographic image group is determined based on continuity between adjacent images, in image features extracted from the high-magnification images. For example, the image feature acquiring unit 136 extracts layer boundaries as image features, by the following procedures. That is to say, the image feature acquiring unit 136 extracts the boundary positions of the inner limiting membrane B1, nerve fiber layer boundary B2, inner plexiform layer boundary B4, photoreceptor inner/outer boundary B5, and retinal pigment epithelium boundary B6, as image features from the wide-angle image D1 stored in the storage unit 120, i.e., from a three-dimensional tomographic image of the eye. The extracted image features are then stored in the storage unit 120.

Now, feature extraction procedures from the wide-angle image D1 will be described in detail. First, the extracting procedures for extracting layer boundaries will be described. The three-dimensional tomographic image to be processed here is conceived as being a set of two-dimensional tomographic images (B-scan images) and the following processing is performed on the two-dimensional tomographic images. First, a two-dimensional tomographic image of interest is subjected to smoothing processing, and noise components are removed. Next, edge components are detected from the two-dimensional tomographic image, and several line segments are extracted as layer boundary candidates based on the continuity thereof. Of the extracted candidates, the uppermost line segment is extracted as the inner limiting membrane B1, the line segment second from the top is extracted as the nerve fiber layer boundary B2, and the third line segment is extracted as the inner plexiform layer boundary B4. The line segment with the largest contrast at the outer retina side from the inner limiting membrane B1 (the size at which the z coordinate is large in FIG. 6A) is extracted as the photoreceptor inner/outer boundary B5. Further, the bottom line segment of the layer boundary candidate group is extracted as the retinal pigment epithelium boundary B6. A deformable model such as Snakes or level sets or the like may be applied for the initial values of the line segments, to extract more precisely. Graph cuts may be used to extract layer boundaries. Boundary extraction using deformable models and graph cuts may be performed three-dimensionally on the three-dimensional tomographic image, or may be performed two-dimensionally on the two-dimensional tomographic images. Any method may be used to extract layer boundaries, as long as capable of extracting layer boundaries from a tomographic image of the eye.

Also, layer boundary extraction from the high-magnification images Dhj_n can be executed based on the relative positions of the wide-angle image D1 and high-magnification images Dhj_n, and layer boundary positions detected from the wide-angle image D1. That is to say, the layers are detected from a wide-angle image D1 correlated with the high-magnification images Dhj_n, and the boundary of the corresponding layers in the high-magnification images Dhj_n can be detected near the position of the layer boundaries detected in the wide-angle image D1.

According to the configuration described above, when compositing and displaying high-magnification adaptive optic OCT tomographic images taken at different shooting positions, the image processing apparatus 10 determines suitability of an image group based on how small an unobservable (unanalyzable) region is within a composited image as compared to a region of shooting (analyzing). Accordingly, in a case where cells and tissue to be analyzed, and lesions thereof, exist across multiple high-magnification images, a composited image which can be analyzed under generally the same conditions can be generated.

Fourth Embodiment

Comparison of Composited Image and Region Shot (Analyzed) in Different Examination The image processing apparatus according to the a fourth embodiment determines suitability of an image group based on how small an unobservable (unanalyzable) region is at the time of compositing and displaying high-magnification adaptive optic SLO images of different shooting positions, in a case of comparing a region shot (analyzed) in a different examination. Specifically, description will be made regarding a case of determining suitability of an image group based on how small an unobservable (unanalyzable) region is in a composited image, when compared with an image group Dhjf (f=1, 2, . . . , n−1) shot in an examination date in the past.

Figure 13:
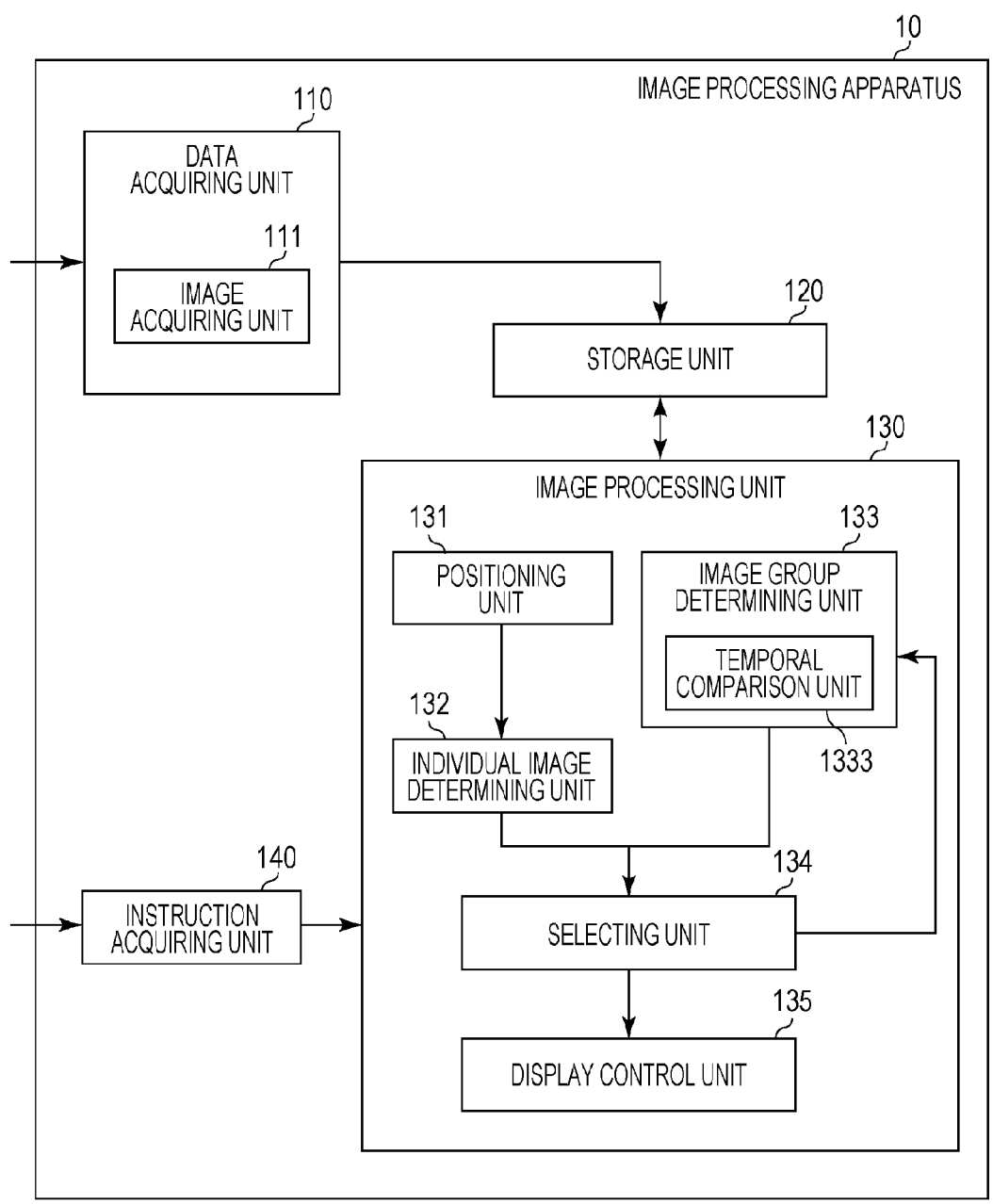
FIG. 13 is a block diagram illustrating a functional configuration example of an image processing apparatus according to a fourth embodiment of the present invention.

The configuration of apparatuses connected with the image processing apparatus 10 according to the present embodiment is the same as in the first embodiment. Next, FIG. 13 illustrates functional blocks of the image processing apparatus 10 according to the present embodiment. This differs from the case in the first embodiment with regard to the point that the image group determining unit 133 is provided with a temporal comparison unit 1333. The image processing flow according to the present embodiment is the same as that in FIG. 5, with S530, S560, S570, and S580 being the same as in the first embodiment. Accordingly, only the processing of S510, S520, S540, and S550 will be described. Note that Dsjf and Fsf each represent cases of acquiring SLO images and fixation targets at different magnifications, different shooting positions, or different examination dates, where s is a variable that represents magnification, j a variable that represents shooting position No., and f a variable that represents examination date, written as s=1, 2, ..., smax, j=1, 2, ..., jmax, and f=1, 2, ..., fmax. The smaller s is, the greater the shooting magnification is (the narrower the angle of view is). The smaller f is, the older the examination date is. The shooting position of the lowest-magnification image (wide-angle image) is one in the present embodiment, and the shooting position No. will be abbreviated for sake of simplicity.

Step 510: Image Acquisition

The image acquiring unit 111 requests the data server 40 to transmit past SLO images Dsjf (f=1, 2, ..., n−1), fixation target positions Fsf, and positioning parameter values corresponding to the SLO images Dsjf. The data server 40 transmits data corresponding to this request to the image processing apparatus 10, and saves in the storage unit 120. In the present embodiment, n=4.

Next, the image acquiring unit 111 requests the SLO image imaging apparatus 20 to acquire newest examination images and fixation target positions, the SLO images Dsjn and fixation target positions Fsn. In the present embodiment, the fixation target positions F2n and F1n are set at the fovea of the macula, and a low-magnification SLO image D2n and high-magnification images D1jn are acquired from the SLO image imaging apparatus 20.

Step 520: Positioning

The positioning unit 131 performs positioning of the wide-angle image D2f (f=1, 2, ..., n) and the high-magnification images D1jf, and obtains the relative position of the high-magnification images D1jf upon the wide-angle image D2f, thereby generating a composited image of the high-magnification wide-angle images D1jf.

In a case where there is an overlapping region among the high-magnification images D1jf from the same examination date, the inter-image similarity is calculated regarding this overlapping region, and positions the high-magnification images D1jf with each other at the position where the inter-image similarity is the greatest. In a case where images of three or more different types of magnification have been acquired, positioning is performed from lower magnification images. For example, in a case where an image D3f, an image D2kf, and an image D1jf have been acquired, first, positioning is performed between the image D3f and image D2kf, and next, positioning is performed between the image D2kf and image D1jf. Further, the positioning unit 131 acquires the fixation target position F1f used for shooting the image D1jf from the storage unit 120, and uses this to set a search start point for a positioning parameter in the positioning between the image D2f and the image D1jf. Any known technique can be used for inter-image similarity or coordinate conversion techniques. In the present embodiment, a correlation coefficient is used for inter-image similarity, and Affine transform is used as the coordinate conversion technique to perform positioning.

Next, the wide-angle image D2n from the newest examination and a wide-angle image D2f (f=1, 2, ..., n−1) from a past examination are positioned. Further, the relative position of a high-magnification image D1jf from a past examination as to a high-magnification image D1jn in the newest examination is obtained using the relative position of the wide-angle image D2n as to the high-magnification image D1jn the relative position of the wide-angle image D2f as to D2n, and the relative position of the high-magnification image D1jf as to D2f. Note that positioning may be directly performed between the high-magnification image D1jn in the newest examination as to the high-magnification image D1jf from a past examination. The positioning unit 131 acquires fixation target positions of the images from the storage unit 120. The positioning unit 131 sets the search start point for positioning of the high-magnification image D1jn of the newest examination and the wide-angle image D2n of the newest examination, D2n and a wide-angle image D2f of a past examination, and D2f and a high-magnification image D1jf of a past examination, using these fixation target positions.

Any technique can be used for the positioning technique. In the present embodiment, Affine transform is used for positioning first, to perform general positioning. Next, fine positioning is performed using the free form deformation (FFD) technique, which is a non-rigid positioning technique. In either positioning, a correlation coefficient is used for inter-image similarity. Of course, any known inter-image similarity may be used, and is not restricted to this. Thus, pixels of the newest examination image (wide-angle image D2n or high-magnification image D1jf) and pixels of a past examination image (wide-angle image D2f or high-magnification image D1jf) are correlated.

The present invention is not restricted to positioning based on similarity of pixel values. For example, the image processing apparatus 10 may be provided with an image feature acquiring unit 136 in the same way as with the second embodiment, with the image feature acquiring unit 136 identifying capillary regions, and positioning then being performed based on features using the identified blood vessel region.

Step 540: Processing to Determine Suitability as Image Group

The image group determining unit 133 determines suitability of an image group based on how small an unobservable (unanalyzable) region is when compared with a region shot (analyzed) in a different examination, the selecting unit 134 selects a composition of images with the highest suitability, and forms a composited image. Assumption will be made in the present embodiment that the image group is made up of nine overlaid images such as illustrated in FIG. 6G, and that the image No. j increases in raster scanning (zigzag scanning) order from the upper left. Determination principles relating to the composited images (image group) are as listed below in order of priority, which are 1. that no incomplete-image region is generated in the composited image, 2. that the image quality does not vary according to the shooting position, and 3. that unobservable (unanalyzable) regions do not readily occur when compared with a region shot (analyzed) in a different examination.

Of these, 1 and 2 are conditions set for enabling within the composited image to be observed under the same conditions. Now, in a case where suitability as an image group is not determined, for example, (i) in a case where the composited image is generated following the principle of (ii) in S730 for each shooting position, there will be cases where the above condition 2 is not satisfied. Also, (ii) in a case where (i) is satisfied and also condition 2 is satisfied, the image quality is lower than a case where suitability of the image group is determined and images are selected, since the number of overlaid images has to match that of the image with the fewest overlaid images. Accordingly, performing suitability determination taking into consideration data continuity and complementation at the edges and overlapping portions of adjacent images enables a higher-quality composited image to be obtained (overlaying being performed with a greater number of images), while satisfying conditions 1 through 3.

In the present embodiment, there are redundant regions between two adjacent images, such as indicated by the gray regions in FIG. 6F, and redundant regions between four adjacent images, such as indicated by the black regions in FIG. 6F. Specifically, the suitability of the image group is determined by the following procedures.

(1) Individual images generated in S530 (priority on image quality) are composited according to the positioning parameters obtained in S520.

(2) The temporal comparison unit 1333 checks whether or not there are incomplete image regions in a case of comparing the composited image generated in (1) with composited images generated in past examinations.

Specifically, a logical disjunction $(\cap_j(\cup_j D1jf)$ is a region of comparison as to the compositing of the image group $D1jf$ of each examination, i.e., as to the logical disjunction $(\cup D1jf)$ of $D1jf$. There are three image groups serving as objects of comparison (different examinations) in the present embodiment, so whether or not there are incomplete-image regions is checked in a case where the region of comparison is a logical disjunction $(\cup D1j1) \cap (\cup_j D1j2) \cap (\cup_j D1j3)$, as to the compositing of the image group $D1jf$ of each examination, i.e., as to $\cup D1jf$.

Accordingly, (area of composited image generated in (1)−area of incomplete images)/(area of composited image generated in (1))

is calculated as the suitability of the image group. Note that the method for setting a region for comparison is not restricted to this; any comparison region may be set. A region for comparison may also be set manually. The selecting unit 134 performs image selection in the high-magnification images so that the suitability is the highest, based on the suitability of the image group, and performs forming processing of an image group based on the selected images. Specifically, image selection is performed according to the following procedures, and image group formation processing is performed.

(3) If there are no incomplete images, the composited image is formed as it is and the processing ends.

(4) If there are incomplete images, the position of the incomplete-image region is obtained.

(5) Check whether or not there is complementary (substitute) data in a redundant region of an image including the incomplete-image region or having a side adjacent to the incomplete-image region. For example, in FIG. 6G there are incomplete images in image 6 and image 9, so whether or not there is complementary data at image 6 and the left edge of image 5, and in image 9, is checked.

(6) If there is complementary (substitute) data, the incomplete image region is replaced with complementary data that has the best image quality (the number of overlaid images is the greatest) of the complementary data, and (8) is executed.

(7) If there is no complementary (substitute) data, selected frames of images having images including incomplete-image regions or a side adjacent to the region are changed so that the incomplete-image region is resolved. If there are multiple frame selection methods to resolve the incomplete-image region, the frame selection method where the number of overlaid images is the greatest is selected.

(8) The number of overlaid images ANmin that is the smallest number of overlaid images out of the overlaid image group obtained in (7) is set as the number of overlaid images of the composited image, the number of overlaid images at each shooting position is changed to ANmin, and the overlaid image is generated again.

(9) The overlaid image generated in (8) is used to generate a composited image. There are no more incomplete images, as illustrated in FIG. 6H, and a composited image where the numbers of overlaid images are the same and are maximal is generated. Note that the forming is performed in the present embodiment based on determination of suitability of the image group.

While the composited image formed based on the determination of suitability as an image group has been described as being a still image (overlaid image) in the present embodiment, the present invention is not restricted to this. For example, suitability determination may be performed taking into consideration complementation of data at the edges and overlapping portions of adjacent moving images, and a moving image may be composited and displayed thereupon, as illustrated in FIG. 6J. The flow of the basic processing in a case of composited display of moving images is the same as in a case of composited display of still images, but the following points differ.

(i) A time phase data acquiring apparatus 50 such as illustrated in FIG. 2B is connected to the image processing apparatus 10, and time phase data is acquired simultaneously with the moving image. Time phase data is biosignal data acquired by a sphygmograph, for example. Referencing the time phase data yields the playback cycle of each moving image. The playback cycle is aligned among the moving images by frame interpolation processing of the moving images (between shooting positions, or between examinations, or both).

(ii) The longest continuous frame section from which frames with abnormal luminesce have been removed is selected in the image formation processing in increments of shooting position.

(iii) Suitability determination is performed in the suitability determination processing for the image group according to the following principle, which is to composite and display moving images with as many frames (pulse cycles) as possible, where the number of playback frames (pulse cycles), in which the number of playback frames (pulse cycles) with no incomplete-image regions occurring in the composited image is generally the same for each shooting position, is generally the same between examinations.

(iv) The frames selected in (6) (7) (8) of the image formation processing as an image group are set as a continuous frame section.

Accordingly, incomplete images are eliminated from the composited display of the moving image, and a composited moving image with the longest continuation of frames having the same number of playback frames is formed. In a case where no time phase data is acquired, a composited display may be made as a moving image without adjusting the playback clock time. Although the above conditions 1 through 3 have been used as suitability for the image group (still image group and moving image group) in the present embodiment, the present invention is not restricted to this; any suitability may be set.

Step 550: Display

The display control unit 135 uses the positioning parameters obtained in S520 and the image group formed in S540 to composite and display the high-magnification images $D1jn$ upon the wide-angle image $D2n$. According to the configuration described above, when compositing and displaying high-magnification adaptive optic SLO images taken at different shooting positions, the image processing apparatus 10 determines suitability of an image group based on how small an unobservable (unanalyzable) region is, in a case of comparing a region shot (analyzed) in a different examination. Accordingly, in a case where cells and tissue to be observed or analyzed, and lesions thereof, exist across multiple high-magnification images, a composited image which can be observed or analyzed under generally the same conditions can be generated.

Other Embodiments

Although a case of shooting one image group and determining suitability has been described in the above embodiments, embodiments of the present invention are not restricted to this. That is to say, in a case where multiple image groups are shot in one examination as illustrated in FIGS. 14A and 14B, images in the image groups may be tentatively selected in the same way as in the above embodiments, after which suitability is determined among the image groups and images are selected based on the suitability among the image groups.

For example, in a case of acquiring adaptive optic SLO images of different magnifications at each shooting position and generating a composited image as illustrated in FIG. 14A, suitability for the image group is determined for each magnification, and images are tentatively selected. Thereafter, determination of suitability may be made among the magnifications (area of logical disjunction of high-magnification image D1$j$ group that does not extend outside of shooting region of low-magnification image D2$k$ group/area of logical disjunction of high-magnification image D1$j$ group), and images may be selected based on the suitability among the image groups.

Also, in a case of having multiple image groups MnDhj (multi-placement type) as illustrated in FIG. 14B, first, suitability is determined within each image group as in the above-described embodiments, and images are tentatively selected. Thereafter, suitability among the image groups is determined based on suitability relating to the luminance properties (e.g., average luminesce or S/N ratio similarity within the image group) among the image groups (e.g., among adjacent image groups), and images may be selected based on the suitability among the image groups. In a multi-placement type, the image groups may be away from each other, may be adjacent, or may be overlapping. Cases where the size of the image group (e.g., number of acquired positions of images making up the image group) differs among image groups are also included in the present invention.

Also, in a case of acquiring image groups of a multi-placement type in multiple magnifications as illustrated in FIG. 14C, either case of first obtaining suitability among image groups with different magnifications and suitability among image groups with different acquisition positions is included in the present invention.

Also, while the images to be positioned in the above described embodiments have been realized as SLO images or tomographic images of the eye, the embodiments of the present invention are not restricted to these. For example, the wide-angle image D1 may be realized as a fundus camera image and the high-magnification image Dh realized as an adaptive optic fundus camera image. Also, the images may be realized as images with different modalities, such as the wide-angle image D1 being a wide-angle SLO image and the high-magnification image Dh being a projected image of an adaptive optic system tomography image, or the wide-angle image D1 being an adaptive optic system tomography image and the high-magnification image being an adaptive optic SLO image. This also may be realized as a configuration where a complex machine of the adaptive optic SLO image imaging apparatus 20 and the tomographic image imaging apparatus 60 is directly connected to the image processing apparatus 10.

Further, while the present invention has been realized as an image processing apparatus in the above-described embodiments, embodiments of the present invention are not restricted just to an image processing apparatus. For example, the present invention may be realized as software executed by a CPU of a computer. It is needless to say that a storage medium storing this software also makes up the present invention.

When selecting images from moving images, at least one of the edges and overlapping portions of multiple images is preferably used. Preferably further provided is a comparing unit to compare a composited image and a wide-angle image that is of a wider angle of view than each of the multiple moving images (e.g., the image group determining unit 133 in FIG. 1). Thus, a determining unit can determine values indicating continuity, based on comparison results by the comparing unit. Preferably further provided is a display control unit (e.g., the display control unit 135 in FIG. 1) for displaying the composited image where the selected images have been composited, on a display unit. Also, blood vessels are preferably automatically (or instructed manually by the user or semi-automatically) extracted from the composited image, with the movement speed and so forth of blood cells in the extracted blood vessels being measured. Note that the multiple images do not have to be composited; each of multiple images may be displayed arrayed on the display unit, or may be switched one at a time and displayed on the display unit.

The present invention is also realized by executing the following processing. That is to say, processing where software (program) that realizes functions of the embodiments described above are supplied to a system or apparatus via network or various types of storage media, and a computer (or CPU or microprocessor unit (MPU) or the like) of the system or apparatus reading out and executing the program.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-181342, filed Sep. 5, 2014, which is hereby incorporated by reference herein in its entirety.

What is claimed is:

1. An image processing apparatus that generates one image by using at least one frame each of a plurality of moving images obtained by taking moving images of a plurality of different regions of an eye at different times, the apparatus comprising:
a deciding unit configured to decide the at least one frame in each of the plurality of moving images, so that regions which have actually been shot are included in the plurality of moving images in the plurality of regions; and
an image generating unit configured to generate one image by using the at least one frames decided from each of the plurality of moving images.

2. The image processing apparatus according to claim 1, wherein the deciding unit decides the at least one frame, so that similarity among the at least one frames in the plurality of moving images is equal to a threshold value or higher.

3. The image processing apparatus according to claim 1, further comprising:
an image acquiring unit communicably connected to an ophthalmologic apparatus, to acquire the plurality of moving images obtained by the ophthalmologic apparatus taking the moving images of the eye.

4. The image processing apparatus according to claim 3, the ophthalmologic apparatus further including
a scanning optical system configured to scan measurement light on the eye;
wherein the image acquiring unit controls the scanning optical system so that the measurement light is repeatedly scanned on the plurality of regions of the eye, thereby acquiring the plurality of moving images.

5. The image processing apparatus according to claim 3, the ophthalmologic apparatus further including
a scanning optical system configured to scan measurement light on the eye;
wherein the image acquiring unit controls a position of a fixation target to fix the eye so that the measurement light is repeatedly scanned on each of the plurality of regions of the eye, thereby acquiring the plurality of moving images.

6. The image processing apparatus according to claim 3, the ophthalmologic apparatus further including
a wavefront correction device configured to correct a wavefront of at least one light of measurement light and returning light from the eye,
wherein the image acquiring unit acquires the plurality of moving images obtained by taking moving images of the eye using light of which the wavefront has been corrected.

7. An image processing apparatus comprising:
an image acquiring unit configured to acquire a plurality of moving images shot at different positions of an eye;
a determining unit configured to determine a value indicating continuity of properties of a plurality of images made up of images obtained by being selected from each of the plurality of acquired moving images;
a selecting unit configured to select images from the plurality of acquired moving images, so that the determined value satisfies a predetermined condition; and
a display control unit configured to display an image generated from the selected images, on a display unit.

8. The image processing apparatus according to claim 7, wherein the determining unit determines a value indicating continuity of at least one of relative position, luminance properties, and image features of the plurality of images.

9. The image processing apparatus according to claim 7, wherein the determining unit determines a value indicating continuity of properties in the plurality of images, in at least one of edges and overlapping regions of the plurality of images.

10. The image processing apparatus according to claim 7, wherein the determining unit determines a value indicating the continuity, based on an image generated from the plurality of images.

11. The image processing apparatus according to claim 7, wherein the determining unit determines a value indicating the continuity, based on at least one of an area of an image generated from the plurality of images, and a length of an avascular area boundary.

12. The image processing apparatus according to claim 7, further comprising:
a comparing unit configured to compare an image generated from the plurality of images, with a wide-angle image which has a wider angle of view than each of the acquired plurality of moving images,
wherein the determining unit determines a value indicating the continuity, based on comparison results from the comparing unit.

13. An image processing apparatus comprising:
an image acquiring unit configured to acquire a plurality of images relating to an eye at different acquiring positions;
a determining unit configured to determine suitability of an image group of the plurality of acquired images; and
a selecting unit configured to select at least one of a region or frame within the images, or images at generally the same acquiring position, based on the determination results from the determining unit.

14. The image processing apparatus according to claim 13, wherein the determining unit determines the suitability of the image group based on at least one of relative position between images of a same examination, continuity of luminance properties, similarity of image quality, and image features of the plurality of acquired images.

15. The image processing apparatus according to claim 13, wherein the determining unit determines the suitability based on at least one of relative position among image groups from different examinations, continuity of luminance properties, and similarity of image quality.

16. The image processing apparatus according to claim 13, further comprising:
a display control unit configured to display one image generated by using regions or frames of images selected by the selecting unit, on a display unit.

17. The image processing apparatus according to claim 13, further comprising:
a measuring unit configured to measure movement speed of blood cells in regions or frames of images selected by the selecting unit.

* * * * *